United States Patent [19]

Eidenschink et al.

[11] Patent Number: 4,986,931
[45] Date of Patent: * Jan. 22, 1991

[54] CYCLOHEXANE DERIVATIVES

[75] Inventors: Rudolf Eidenschink, Dieburg; Günther Haas, Neckargemünd; Ludwig Pohl, Darmstadt; Michael Römer, Rodgau; Bernhard Scheuble, Alsbach; Georg Weber, Erzhausen, all of Fed. Rep. of Germany

[73] Assignee: Merck Patent Gesellschaft mit beschränkter Haftung, Darmstadt, Fed. Rep. of Germany

[*] Notice: The portion of the term of this patent subsequent to Apr. 9, 2002 has been disclaimed.

[21] Appl. No.: 53,908

[22] Filed: May 26, 1987

Related U.S. Application Data

[60] Division of Ser. No. 12,691, Feb. 9, 1987, which is a division of Ser. No. 700,860, Feb. 12, 1985, abandoned, which is a division of Ser. No. 526,927, Aug. 26, 1983, Pat. No. 4,510,069, and Ser. No. 35,548, Apr. 7, 1987, which is a continuation of Ser. No. 705,811, Feb. 26, 1985, abandoned, which is a continuation-in-part of Ser. No. 526,927, Aug. 26, 1983, Pat. No. 4,510,069.

[30] Foreign Application Priority Data

Aug. 26, 1982 [DE] Fed. Rep. of Germany ....... 3231707
Jun. 3, 1983 [DE] Fed. Rep. of Germany ....... 3320024
Feb. 27, 1984 [DE] Fed. Rep. of Germany ....... 3407013

[51] Int. Cl.$^5$ ............................................. C09K 19/30
[52] U.S. Cl. .......................... 252/299.63; 252/299.01; 252/299.61; 252/299.62
[58] Field of Search ...................... 252/299.01, 299.61, 252/299.62, 299.63, 299.5; 350/350 R

[56] References Cited

U.S. PATENT DOCUMENTS 4,629,581 12/1986 Petrzilka et al. ............... 252/299.63
4,659,499 4/1987 Ferrato ........................... 252/299.63

Primary Examiner—John S. Maples
Assistant Examiner—Richard Treauor
Attorney, Agent, or Firm—Millen, White & Zelano

[57] ABSTRACT

Cyclohexane derivatives of formula I $$R^1-(A^1)_m-Z^1-A-Z^2-(A^2)_n-R^2 \qquad (I)$$

wherein $R^1$ and $R^2$ are each H, an alkyl group which has 1–10 C atoms and in which one or two $CH_2$ groups can also be replaced by O atoms, F, Cl, Br, CN or —O—COR, $A^1$ and $A^2$ are each 1,4-phenylene, 1,4-cyclohexylene, 1,3-dioxane-2,5-diyl, piperidine-1,4-diyl, 1,4-bicyclo(2,2,2)-octylene or pyrimidine-2,5-diyl groups which are unsubstituted or substituted by 1–4 F atoms, A is a 1,4-cyclohexylene group which is substituted in the 1-position and/or 4-position by alkyl, alkoxy, fluorinated alkyl or fluorinated alkoxy, each of which has 1–5 C atoms, F, Cl, Br and/or CN and which can also carry 1 or 2 further F, Cl or Br atoms and/or CN groups, $Z^1$ and $Z^2$ are each —CO—O—, —O—CO—, —$CH_2$$CH_2$—, —$OCH_2$—, —$CH_2O$— or a single bond, R is an alkyl group which has 1–5 C atoms, m is 1 or 2 and n is 0 or 1, it being possible, where m=2, for the two groups $A^1$ to be identical or different from one another; and the acid addition salts of those compounds which are basic, are suitable for use as components of liquid-crystal dielectrics.

4 Claims, No Drawings

CYCLOHEXANE DERIVATIVES

This is a division of application SN 012,691 of Feb. 9, 1987, which is a division of SN 700,860 of Feb. 12, 1985 abandoned, which is a division of SN 526,927 of Aug. 26, 1983, now U.S. Pat. No. 4,510,069; and also of SN 035,548 of Apr. 7, 1987, which is a continuation of 705,811 of Feb. 26, 1985 abandoned, which is a continuation in part of 526,927 of Aug. 26, 1983 now U.S. Pat. No. 4,510,069.

SUMMARY OF THE INVENTION

It is an object of this invention to provide compounds useful in liquid crystalline applications, e.g., mesogenic compounds useful in liquid crystalline dielectrics.

Upon further study of the specification and appended claims, further objects and advantages of this invention will become apparent to those skilled in the art.

These objects have been attained by providing cyclohexane derivatives of formula I

wherein $R^1$ and $R^2$ are each independently H; alkyl of 1-10 C atoms in which one or two $CH_2$ groups can optionally be replaced by O atoms; F; Cl; Br; CN; or —O—COR;

$A^1$ and $A^2$ are each independently 1,4-phenylene, 1,4-cyclohexylene, 1,3-dioxane-2,5-diyl, piperidine-1,4-diyl, 1,4-bicyclo(2,2,2)-octylene or pyrimidine-2,5-diyl, each of which is unsubstituted or substituted by 1-4 F atoms;

A is 1,4-cyclohexylene which is substituted in the 1-position and/or 4-position by alkyl, alkoxy, fluorinated alkyl or fluorinated alkoxy, each of which has 1-5 C atoms, F, Cl, Br and/or CN and which can also carry 1 or 2 additional F, Cl or Br atoms and/or CN groups;

$Z^1$ and $Z^2$ are each independently —CO—O—, —O—CO—, —$CH_2CH_2$—, —$OCH_2$—, —$CH_2O$— or a single bond;

R is alkyl of 1-5 C atoms, m is 1 or 2 and n is 0 or 1, wherein when m is 2, the two $A^1$ groups can be identical or different from one another;

and the acid addition salts of such compounds which are basic.

For the sake of simplicity, in the following text "Phe" is 1,4-phenylene, "Cy" is 1,4-cyclohexylene, "Dio" is 1,3-dioxane-2,5-diyl, "Bic" is bicyclo(2,2,2)octylene, "Pip" is piperidine-1,4-diyl and "Pyr" is pyrimidine-2,5-diyl. These notations include the possibility that each of these groups, particularly the 1,4-phenylene group, is unsubstituted or substituted by 1-4 fluorine atoms.

DETAILED DISCUSSION

Similar compounds are known, for example, from European Laid-Open Specification 19,665. However, in contrast, the compounds of this invention contain 1,1,4-trisubstituted cyclohexane rings.

Like similar compounds, the compounds of formula I can be used as components of liquid-crystal dielectrics, in particular for displays based on the principle of the twisted cell, the guest-host effect, the effect of the deformation of aligned phases or the effect of dynamic scattering.

It has been found that the compounds of formula I are excellently suitable for use as components of liquid-crystal dielectrics. In particular, it is possible to use them to prepare stable, liquid-crystal phases which have a strongly negative dielectric anisotropy and thus a low threshold or control voltage for electro-optical effects, a very low optical anisotropy and a comparatively low viscosity.

Surprisingly, it has been found that, when compounds of the formula I are added to mixtures having positive dielectric anisotropy, even fairly large added quantities (for example quantities of 30%) only increase the threshold voltage to a negligible extent. At the same time, a considerable improvement in the steepness of the characteristic curve of the mixture takes place, completely unexpectedly, so that compounds of the type I can be regarded as substances which are particularly advantageously suitable for the preparation of liquid-crystal mixtures which have a steep characteristic curve. They thus make possible the development of highly multiplexable mixtures which have a very low optical anisotropy and by means of which a twisted cell can be operated, particularly in the first Gooch-Tarry transition minimum. This results in the contrast having a very low dependence on the angle of observation.

In addition, the provision of the compounds of the formula I broadens considerably, in a very general way, the range of liquid-crystal substances which are suitable, from various aspects of applied technology, for the preparation of nematic mixtures.

The compounds of the formula I have a wide field of use. Depending on the choice of substituents, these compounds can be used as the base materials of which liquid-crystal dielectrics are mainly composed; it is also possible, however, to add to compounds of the formula I liquid-crystal base materials belonging to other classes of compounds, in order, for example, to reduce the dielectric and/or optical anisotropy of such a dielectric. The compounds of formula I are also suitable as intermediate products for the preparation of other substances which can be used as constituents of liquid-crystal dielectrics.

In the pure state, the compounds of formula I are colorless and form liquid-crystal mesophases in a temperature range which is advantageously situated for electro-optical use. They are very stable to chemicals, heat and light.

This invention also relates to the use of the compounds of the formula I as components of liquid-crystal dielectrics, to liquid-crystal dielectrics containing at least one compound of formula I, and to electro-optical display elements containing dielectrics of this type.

In the preceding and following text, unless indicated expressly to the contrary, $R^1$, $R^2$, $A^1$, $A^2$, A, $Z^1$, $Z^2$, m and n have the meanings indicated above.

The compounds of formula I accordingly embrace compounds of the partial formulae Ia (containing two rings), Ib and Ic (containing three rings in each case) and Id (containing four rings):

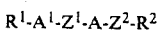     Ia

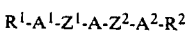     Ib

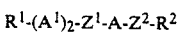     Ic $R^1-(A^1)_2-Z^1-A-Z^2-A^2-R^2$   Id.

The preferred compounds of the partial formula Ia embrace those of the partial formulae Ie to Ij:

$R^1$-Phe-$Z^1$-A-$Z^2$-$R^2$   Ie $R^1$-Cy-$Z^1$-A-$Z^2$-$R^2$   If $R^1$-Dio-$Z^1$-A-$Z^2$-$R^2$   Ig $R^1$-Pip-$Z^1$-A-$Z^2$-$R^2$   Ih $R^1$-Bic-$Z^1$-A-$Z^2$-$R^2$   Ii $R^1$-Pyr-$Z^1$-A-$Z^2$-$R^2$   Ij

Amongst these, those of the formulae Ie, If and Ig are particularly preferred.

Amongst the compounds of the partial formulae Ib, Ic and Id, those of the partial formulae Ik to Iz are particularly preferred:

$R^1$-Phe-$Z^1$-A-$Z^2$-Phe-$R^2$   Ik $R^1$-Dio-$Z^1$-A-$Z^2$-Cy-$R^2$   Il $R^1$-Cy-$Z^1$-A-$Z^2$-Phe-$R^2$   Im $R^1$-Cy-$Z^1$-A-$Z^2$-Cy-$R^2$   In $R^1$-Phe-Phe-$Z^1$-A-$Z^2$-$R^2$   Io $R^1$-Phe-Cy-$Z^1$-A-$Z^2$-$R^2$   Ip $R^1$-Cy-Phe-$Z^1$-A-$Z^2$-$R^2$   Iq $R^1$-Cy-Cy-$Z^1$-A-$Z^2$-$R^2$   Ir $R^1$-Phe-Phe-$Z^1$-A-$Z^2$-Phe-$R^2$   Is $R^1$-Phe-Phe-$Z^1$-A-$Z^2$-Cy-$R^2$   It $R^1$-Phe-Cy-$Z^1$-A-$Z^2$-Phe-$R^2$   Iu $R^1$-Phe-Cy-$Z^1$-A-$Z^2$-Cy-$R^2$   Iv $R^1$-Cy-Phe-$Z^1$-A-$Z^2$-Phe-$R^2$   Iw $R^1$-Cy-Phe-$Z^1$-A-$Z^2$-Cy-$R^2$   Ix $R^1$-Cy-Cy-$Z^1$-A-$Z^2$-Phe-$R^2$   Iy $R^1$-Cy-Cy-$Z^1$-A-$Z^2$-Cy-$R^2$   Iz

In the compounds of the formulae given above and below, $R^1$ and $R^2$ are preferably alkyl and also alkoxy (especially when these radicals are on a Phe group) or another oxaalkyl group.

$A^1$ and $A^2$ are preferably Cy or Phe and also preferably Dio or Pip; the compound of the formula I preferably does not contain more than one of the radicals Dio, Pip, Bic or Pyr.

A is preferably a 1-X-1,4-cyclohexylene group which does not carry further substituents and in which X is alkyl, alkoxy, fluorinated alkyl or fluorinated alkoxy, each of which has 1-5 C atoms, F, Cl, Br or CN. A CN, $CH_3$, $CH_3O$ or $CF_3$ group is preferred.

$Z^1$ and $Z^2$ are preferably single bonds; as a second preference they are —CO—O— or —O—CO— groups.
m is preferably 1; n is preferably 0.

If $R^1$ and/or $R^2$ are alkyl radicals in which one ("alkoxy" or "oxaalkyl") or two ("alkoxyalkoxy" or "dioxaalkyl") $CH_2$ groups can also be replaced by O atoms, they can be linear or branched. Preferably, they are linear and have 2, 3, 4, 5, 6 or 7 C atoms and are, accordingly, preferably ethyl, propyl, butyl, pentyl, hexyl, heptyl, ethoxy, propoxy, butoxy, pentoxy, hexoxy, heptoxy, 2-oxapropyl (=methoxymethyl), 2-oxabutyl (=ethoxymethyl)- or 3-oxabutyl (=2-methoxyethyl), 2-, 3- or 4-oxapentyl, 2-, 3-, 4- or 5-oxahexyl or 2-, 3-, 4-, 5- or 6-oxaheptyl, also methyl, octyl, nonyl, decyl, methoxy, octyloxy, nonyloxy, decyloxy, 2-, 3-, 4-, 5-, 6-or 7-oxaoctyl, 2-, 3-, 4-, 5-, 6-, 7- or 8-oxanonyl, 2-, 3-, 4-, 5-, 6-, 7-, 8-, or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl.

Compounds of the formulae I and Ia to Iap having branched wing groups $R^1$ and $R^2$ can occasionally be of importance because of improved solubility in the customary liquid-crystal base materials, but are especially of importance as chiral doping agents, if they are optically active. Branched groups of this type do not, as a rule, contain more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

In the radicals R and X, the alkyl groups or alkoxy groups, respectively, are also preferably linear and are, in particular, methyl or ethyl, and also propyl, butyl or pentyl, X being also methoxy or ethoxy, and also propoxy, botoxy or pentoxy.

Preferred compounds amongst those of the formulae I and Ia to Iz are those in which at least one of the radicals contained therein has one of the preferred meanings indicated. Particularly preferred smaller groups of compounds are those of the formulae Iaa to Iat:

$R^1-A^1-Z^1-A-R^2$   Iaa $R^1$-Phe-$Z^1$-A-$R^2$   Iab $R^1$-Phe-A-$R^2$   Iac $R^1$-Phe-CO-O-A-$R^2$   Iad $R^1$-Phe-O-CO-A-$R^2$   Iae $R^1$-Phe-$CH_2CH_2$-A-$R^2$   Iaf $R^1$-Phe-O-$CH_2$-A-$R^2$   Iag $R^1$-Phe-$CH_2$-O-A-$R^2$   Iah $R^1$-Cy-$Z^1$-A-$R^2$   Iai $R^1$-Cy-A-$R^2$   Iaj $R^1$-Cy-CO-O-A-$R^2$   Iak $R^1$-Cy-O-CO-A-$R^2$   Ial $R^1$-Cy-$CH_2CH_2$-A-$R^2$   Iam $R^1$-Cy-O-$CH_2$-A-$R^2$   Ian

| | |
|---|---|
| $R^1$-Cy-$CH_2$-O-A-$R^2$ | Iao |
| $R^1$-Dio-A-$R^2$ | Iap |
| $R^1$-Pip-A-$R^2$ | Iaq |
| $R^1$-Bic-A-$R^2$ | Iar |
| $R^1$-Pyr-A-$R^2$ | Ias |
| $R^1$-Phe-Phe-A-$R^2$ | Iat. |

In the compounds of the formulae mentioned above, the group A contains a substituent X which can be in the 1-position or in the 4-position. Thus the compounds of the formula I include, for example, the compounds of the partial formulae I' and I" below

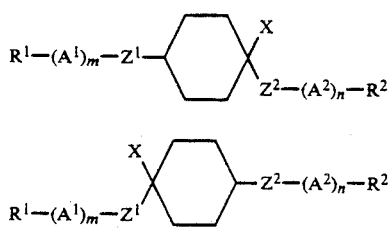

(wherein the cyclohexane ring can, in addition, carry a further substituent X in the opposite position (the 4-position or the 1-position, respectively) of the cyclohexane ring and also 1 or 2 further F, Cl or Br atoms and/or CN groups).

In this respect, compounds of the formulae I and Ia to Iat indicated which are also particularly preferred are those in which the radical A is, in each case:

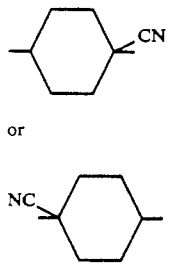

In theses formulae, preferred stereoisomers are those in which the groups $R^1$-$(A^1)_m$-$Z^1$- and -$Z^2$-$(A^2)_n$-$R^2$ are in the trans-position in relation to one another, while the substituent X is in the cis-position in relation to the group opposite to it. Thus, for example, the following stereoisomers of the compounds of the formula I' are preferred:

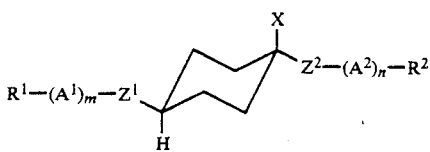

Those of the formulae mentioned above which contain one or more of the groups Dio, Pip and/or Pyr include, in each case, the two possible 2,5-position isomers and 1,4-position isomers. Thus, for example, the partial formula Iap includes the 2-$R^1$-5-(A-$R^2$)-1,3-dioxanes and the 2-(A-$R^2$)-5-$R^1$-1,3-dioxanes, while the partial formula Iaq includes the 1-$R^1$-4-(A-$R^2$)-piperidines and the 1-(A-$R^2$)-4-$R^1$-piperidines.

Compounds of the formulae I, Ia to Iz and Iaa to Iat wherein $R^1$ and $R^2$ are each a straight chain or a branched alkyl group which has 1-10 C atoms and does not contain more than one chain branching and in which one or two $CH_2$ groups can also be replaced by O atoms; F; Cl; Br; CN; or —O—CO—R; and $A^1$, $A^2$, A, $Z^1$, $Z^2$, R, m and n have the meanings given for formula I, are particularly preferred. Most preferred are such compounds further having the above-discussed preferred structural features.

The compounds of formula I can be prepared by methods which are in themselves known, such as are described in the literature (for example in the standard works, such as Houben-Weyl, Methoden der Organischen Chemie ("Methods of organic chemistry"), Georg-Thieme-Verlag, Stuttgart) namely under reaction conditions which are known and suitable for the reactions mentioned. In these reactions, it is also possible to make use of variants which are in themselves known, but are not mentioned here in greater detail.

For example, a process for the preparation of the compounds of this invention comprises, treating a compound which otherwise corresponds to formula I, but contains one or more reducible groups and/or C—C bonds instead of H atoms, with a reducing agent, or adding a compound of the formula HX (wherein X is F, Cl, Br or CN) onto a compound which otherwise corresponds to formula I but contains, instead of the radical A, a 1-cyclohexene-1,4-diyl group which can carry 1 or 2 further F, Cl or Br atoms and/or CN groups, or, in order to prepare esters of formula I (wherein $R^1$ and/or $R^2$ are —O—COR and/or wherein $Z^1$ and/or $R^2$ are —CO—O— or —O—CO—), reacting a corresponding carboxylic acid or one of its reactive derivatives with a corresponding alcohol or one of its reactive derivatives, or, in order to prepare dioxane derivatives of formula I (wherein $A^1$ and/or $A^2$ are 1,3-dioxane-2,5-diyl), reacting a corresponding aldehyde with a corresponding diol, or, in order to prepare nitriles of formula I (wherein $R^1$ and/or $R^2$ are CN and/or wherein A is substituted by at least one CN group), dehydrating a corresponding carboxamide or reacting a corresponding carboxylic acid halide with sulfamide, or, in order to prepare nitriles of formula I (wherein A is a 1,4-cyclohexylene group which is substituted in the 1-position by CN), reacting an acetonitrile of formula II

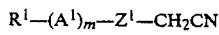

wherein $R^1$, $A^1$, $Z^1$ and m are as defined above, with a compound of formula III

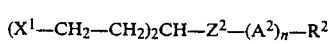

wherein $X^1$ is Cl, Br, I, OH or a reactive esterified OH group and $R^2$, $A^2$, $Z^2$ and n are as defined above, or, in order to prepare nitriles of formula I (wherein A is 1,4-cyclohexylene which is substituted in the 1-position or 4-position by CN and which can be substituted additionally by one or two F atoms and/or CN groups, and wherein, additionally, one of the radicals $Z^1$ or $Z^2$ is a single bond), reacting a nitrile of formula IV $$Q^1-A^3CN \qquad \qquad IV$$

wherein $Q^1$ is
(a) $R^1-(A^1)_m-Z^1-$ or
(b) $R^2-(A^2)_n-Z^2-$ and $A^3$ is a 1,4-cyclohexylene group which is unsubstituted or monosubstituted or disubstituted by F and/or CN, and $R^1$, $R^2$, $A^1$, $A^2$, $Z^1$, $Z^2$, m and n are as defined above, with a compound of formula V $$Q^2-X^1 \qquad \qquad V$$

wherein $Q^2$ is
(a) $R^2-(A^2)_n-$ or
(b) $R^1-(A^1)_m-$ and
$X^1$, $R^1$, $R^2$, $A^1$, $A^2$, m and n are as defined above, or, in order to prepare ethers of formula I (wherein $R^1$ and/or are alkyl in which one or two CH$_2$ groups are replaced by O atoms and/or $Z^1$ and/or $Z^2$ are —OCH$_2$— or —CH$_2$O—, etherifying a corresponding hydroxy compound, or, in order to prepare compounds of formula I containing CF$_3$ groups, reacting a corresponding carboxylic acid with SF$_4$, and/or, optionally reacting a chlorine or bromine compound of formula I (wherein $R^1$ and/or $R^2$ are Cl or Br and/or wherein A is substituted by at least one chlorine or bromine atom) with a cyanide, and/or, optionally, converting a base of formula I into one of its acid addition salts by treatment with an acid, or, optionally, liberating a compound of the formula I from one of its acid addition salts by treatment with a base.

$X^1$ is preferably Cl or Br, but is also I, OH or reactive esterified OH, such as alkylsulfonyloxy having, in particular, 1–6 C atoms (for example methylsulfonyloxy) or arylsulfonyloxy having, in particular, 6–10 C atoms (for example phenylsulfonyloxy, p-tolylsulfonyloxy or naphthylsulfonyloxy).

The starting materials can, if desired, also be formed in situ, in such a manner that they are not isolated from the reaction mixture, but are immediately reacted further to give the compounds of formula I.

Thus, the compounds of formula I can be prepared by reducing a compound which otherwise corresponds to formula I, but contains one or more reducible groups and/or C—C bonds instead of H atoms.

Suitable reducible groups are preferably carbonyl groups, especially keto groups, and also, for example, free or esterified hydroxyl groups or aromatically linked halogen atoms. Preferred starting materials for the reduction correspond to the formula I, but can contain a cyclohexene ring or cyclohexanone ring instead of a cyclohexane ring, and/or a —CH=CH— group, instead of a —CH$_2$CH$_2$— group and/or a —CO— group instead of a —CH$_2$— group, and/or a free or functionally modified OH group (for example in the form of the p-toluenesulfonate of the latter) instead of an H atom.

The reduction can, for example, be effected by means of catalytic hydrogenation at temperatures between about 0° and about 200° and under pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO$_2$ or PtO), on a support (for example Pd on charcoal, calcium carbonate or strontium carbonate) or in a finely divided form.

Ketones can also be reduced by the Clemmensen method (using zinc, amalgamated zinc or tin and hydrochloric acid, preferably in an aqueous alcoholic solution or in a heterogeneous phase using water/toluene at temperatures between about 80° and 120°) or the Wolff-Kishner method (using hydrazine, preferably in the presence of an alkali, such as KOH or NaOH, in a high-boiling solvent, such as diethylene glycol or triethylene glycol, at temperatures between about 100° and 200°) to give the corresponding compounds of the formula I which contain alkyl groups and/or —CH$_2$CH$_2$— bridges.

Reductions by means of complex hydrides are also possible. For example, arylsulfonyloxy groups can be removed by reduction with LiAlH$_4$, in particular p-toluenesulfonyloxymethyl groups can be reduced to methyl groups, preferably in an inert solvent, such as diethyl ether or THF, at temperatures between about 0° and 100°. Double bonds can be hydrogenated (even in the presence of CN groups!) by means of NaBH$_4$ or tributyltin hydride in methanol; thus, for example, the corresponding cyclohexane derivatives are formed from 1-cyanocyclohexene derivatives.

Compounds of the formula I can also be obtained by adding on a compound of the formula HX (hydrogen fluoride, hydrogen chloride, hydrogen bromide or hydrogen cyanide) to an appropriate cyclohexene derivative (which corresponds to the formula I, but contains, instead of the radical A, a 1-cyclohexene-1,4-diyl group which can carry 1 or 2 further F, Cl or Br atoms and/or CN groups).

This addition reaction is carried out, for example, in the presence of an inert solvent, for example a halogenated hydrocarbon, such as CH$_2$Cl$_2$ or CHCl$_3$, a nitrile, such as acetonitrile, or an amide, such as dimethylformamide (DMF), at temperatures between about —10° and +150° and pressures between about 1 and 100 bar. It can be advantageous to add catalysts, for example an addition reaction with HCN can be catalysed by adding palladium bis-[2,3-O-isopropylidene-2,3-dihydroxy-1,4-bis-(diphenylphosphino)-butane].

Esters of the formula I ($R^1$ and/or $R^2$=—O—COR or $Z^1$ and/or $Z^2$=—CO—O— or —O—CO—) can also be obtained by esterifying corresponding carboxylic acids of the formulae R—COOH, $R^1-(A^1)_m$—COOH, $R^1-(A^1)_m-Z^1$—A—COOH, $R^2-(A^2)_n$—COOH or $R^2-(A^2)_n-Z^2$—A—COOH (or reactive derivatives thereof) with alcohols or phenols of the formulae $R^1-(A^1)_m-Z^1$—A—$Z^2-(A^2)_n$—OH, $R^2-(A^2)_n-Z^2$—A—$Z^1-(A^1)_m$—OH, $R^2-(A^2)_n-Z^2$—A—OH, $R^2-(A^2)_n$—OH, $R^1-(A^1)_m-Z^1$—A—OH or $R^1-(A^1)_m$—OH (or reactive derivatives thereof).

Suitable reactive derivatives of the carboxylic acids mentioned are, in particular, the acid halides, above all the chlorides and bromides, and also the anhydrides, for example also mixed anhydrides of the formulae $R^1-(A^1)_m$—CO—O—COCH$_3$, $R^1-(A^1)_m-Z^1$—A—CO—O—COCH$_3$, $R^2-(A^2)_n$—CO—O—COCH$_3$ and $R^2-(A^2)_n-Z^2$—A—CO—O—COCH$_3$, azides or esters, in particular alkyl esters having 1–4 C atoms in the alkyl group.

Suitable reactive derivatives of the alcohols and phenols mentioned are, in particular, the corresponding metal alcoholates or phenates, respectively, of the formulae $R^1-(A^1)_m-Z^1-A-Z^2-(A^2)_n-OM$, $R^2-(A^2)_n-Z^2-A-Z^1-(A^1)_m-OM$, $R^2-(A^2)_n-Z^2-A-OM$, $R^2-(A^2)_n-OM$, $R^1-(A^1)_m-Z^1-A-OM$ and $R^1-(A^1)_m-OM$ wherein M is one equivalent of a metal, preferably an alkali metal, such as Na or K.

It is advantageous to carry out the esterification in the presence of an inert solvent. Solvents which are very suitable are, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, and sulfoxides, such as dimethyl sulfoxide or sulfolane. It can be advantageous to add water-immiscible solvents at the same time in order to remove, by azeotropic distillation, the water formed in the esterification. Occasionally, an excess of an organic base, for example pyridine, quinoline or triethylamine, can also be used as the solvent for the esterification. The esterification can also be carried out in the absence of a solvent, for example by merely heating the components in the presence of sodium acetate. The reaction temperature is usually between −50° and +250°, preferably between −20° and +80°. At these temperatures the esterification reactions are usually complete after 15 minutes to 48 hours.

In an individual case, the reaction conditions for the esterification depend largely on the nature of the starting materials used. Thus, a free carboxylic acid is, as a rule, reacted with a free alcohol or phenol in the presence of a strong acid, for example a mineral acid, such as hydrochloric acid or sulfuric acid. A preferred mode of reaction is to react an acid anhydride or, in particular, an acid chloride with an alcohol, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol or phenol to the sodium or potassium alcoholate or phenate, respectively, for example by treatment with ethanolic sodium hydroxide or potassium hydroxide solution, isolating this alcoholate or phenate and suspending it, together with sodium bicarbonate or potassium carbonate, by stirring in acetone or diethyl ether, and adding a solution of the acid chloride or anhydride in diethyl ether, acetone or DMF to this suspension, preferably at temperatures between about −25° and +20°.

Dioxane derivatives of the formula I (wherein one of the groups $A^1$ and/or $A^2$ is a 1,3-dioxane-2,5-diyl group) are preferably prepared by reacting a corresponding aldehyde, for example of the formulae $R^1-(A^1)_{m-1}-CHO$, $R^1-(A^1)_m-Z^1-A-Z^2-CHO$, $O=CH-(A^1)_{m-1}-Z^1-A-Z^2-(A^2)_n-R^2$ or $O=CH-R^2$ (or a reactive derivative thereof) with a corresponding 1,3-diol, for example of the formulae $(HOCH_2)_2CH-(A^1)_{m-1}-Z^1-A-Z^2-(A^2)_n-R^2$, $(HOCH_2)_2CH-R^2$, $R^1-(A^1)_{m-1}-CH(CH_2OH)_2$ or $R^1-(A^1)_m-Z^1-A-Z^2-CH(CH_2OH)_2$ (or a reactive derivative thereof), preferably in the presence of an inert solvent, such as benzene or toluene, and/or of a catalyst, for example a strong acid, such as sulfuric acid, benzenesulfonic acid or p-toluenesulfonic acid, at temperatures of about 20° to about 150°, preferably 80° to 120°. Suitable reactive derivatives of the starting materials are primarily acetals, for example of the formulae $R^1-(A^1)_{m-1}-CH(OR^3)_2$, $R^1-(A^1)_m-Z^1-A-Z^2-CH(OR^3)_2$, $(R^3O)_2CH-(A^1)_{m-1}-Z^1-A-Z^2-(A^2)_n-R^2$, $(R^3O)_2-R^2$, $R^4-CH(OCH_2)_2-CH-(A^1)_{m-1}-Z^1-A-Z^2-(A^2)_n-R^2$, $R^4-CH(OCH_2)_2CH-R^2$, $R^1-(A^1)_{m-1}-CH(CH_2O)_2CH-R^4$ or $R^1-(A^1)_m-Z^1-A-Z^1-CH(CH_2O)_2CHR^4$ wherein $R^3$ is alkyl of 1–4 C atoms, two radicals $R^3$ together are also alkylene of 2 or 3 C atoms and $R^4$ is H, alkyl of 1–4 C atoms or phenyl.

The aldehydes and 1,3-diols, and also their reactive derivatives, are in some cases known; in all cases they can be prepared without difficulty by standard methods of organic chemistry from compounds which are known from the literature. For example, the aldehydes are obtainable by oxidising corresponding alcohols or by reducing corresponding carboxylic acids or derivatives thereof, and the diols are obtainable by reducing corresponding diesters.

Corresponding acid amides, for example amides in which a $CONH_2$ group is present instead of the radical X, can be dehydrated in order to prepare nitriles of the formula I (wherein $R^1$ and/or $R^2$ are CN and/or wherein A is substituted by at least one CN group). The amides are obtainable, for example, from corresponding esters or acid halides by reacting these with ammonia. Examples of suitable dehydrating agents are inorganic acid chlorides, such as $SOCl_2$, $PCl_3$, $PCl_5$, $POCl_3$, $SO_2Cl_2$ or $COCl_2$, and also $P_2O_5$, $P_2S_5$ and $AlCl_3$ (for example in the form of the double compound with NaCl) and aromatic sulfonic acids and sulfonic acid halides. This reaction can be carried out in the presence or absence of an inert solvent at temperatures between about 0° and 150°; examples of suitable solvents are bases, such as pyridine or triethylamine, aromatic hydrocarbons, such as benzene, toluene or xylene, or amides, such as DMF.

The abovementioned nitriles of the formula I can also be prepared by reacting corresponding acid halides, preferably the chlorides, with sulfamide, preferably in an inert solvent, such as tetramethylene sulfone, at temperatures between about 80° and 150°, preferably at 120°. After working up in a customary manner, the nitriles can be isolated without further treatment.

Nitriles of the formula I wherein A is a 1,4-cyclohexylene group which is substituted in the 1-position by CN are also obtainable by alkylating acetonitriles of the formula II with 1,5-di-$X^1$-pentane derivatives of the formula III. The acetonitriles are obtainable, for example, from corresponding halides of the formula $R^1-(A^1)_m-Z^1-CH_2X^1$ and metal cyanides; the compounds III are accessible by reducing corresponding glutaric acid diesters to give the corresponding diols (III, $X^1=OH$) and also, if appropriate, by reacting the latter with inorganic halides, such as $SOCl_2$, HBr or HI. The acetonitrile is preferably first converted, by means of a strong base, such as NaH, $NaNH_2$, lithium diisopropylamide, piperidide or 2,5-diisopropylpiperidide or K tert.-butylate, into the corresponding carbanion, preferably in an inert solvent, for example a hydrocarbon, such as toluene, an ether, such as THF or dioxane, an amide, such as DMF, a sulfoxide, such as dimethyl sulfoxide, or a mixture of such solvents. After III (wherein $X^1$ is other than OH) has been added, it is preferable to maintain a temperature between 0° and 150° for 0.5 to 16 hours. On the other hand, the reaction of II with III ($X^1$=OH) is preferably effected in the presence of azodicarboxylic acid esters/triphenylphosphine in THF at temperatures between about −30° and +30°.

Nitriles of the formula I wherein A is a 1,4-cyclohexylene group which is substituted in the 1-position or 4-position by CN and which can additionally be substituted by 1-2 F atoms and/or CN groups, are obtainable in a completely analogous manner by reacting a nitrile of the formula IV with a halide of the formula V. The nitriles of the formula IV are obtainable, for example, from corresponding amides of the formula $Q^1$—$A^3$—$CONH_2$ by dehydration, while the halides of the formula V are obtainable from corresponding alcohols of the formula $Q^2$—OH.

Ethers of the formula I (wherein $R^1$ and/or $R^2$ are an alkyl group in which one or two $CH_2$ groups are replaced by O atoms and/or wherein $Z^1$ and/or $Z^2$ are a —$OCH_2$— or a —$CH_2O$— group) are obtainable by etherifying corresponding hydroxy compounds, preferably corresponding phenols, the hydroxy compound being preferably first converted into a corresponding metal derivative, for example into the corresponding alkali metal alcoholate or alkali metal phenate by treatment with NaH, $NaNH_2$, NaOH, KOH, $Na_2CO_3$ or $K_2CO_3$. This metal derivative can then be reacted with the corresponding alkyl halide or sulfonate or dialkyl sulfate, preferably in an inert solvent, such as acetone, 1,2-dimethoxyethane, DMF or dimethyl sulfoxide, or in an excess of aqueous or aqueous alcoholic NaOH or KOH, at temperatures between about 20° and 100°.

Compounds of the formula I containing $CF_3$ groups can be prepared by reacting corresponding carboxylic acids, which, in turn, are obtainable, for example, by hydrolysing corresponding nitriles, can be reacted with $SF_4$, preferably using an excess of $SF_4$ under pressure in the absence, or in the presence, of an inert solvent, such as cyclohexane or methylene dichloride at temperatures between about 70° and 200°. The reaction times vary between about 2 hours and about 4 days.

Nitriles of the formula I (wherein $R^1$ and/or $R^2$ are CN and/or wherein A is substituted by at least one CN group) can also be prepared by reacting corresponding chlorine or bromine compounds of the formula I (wherein $R^1$ and/or $R^2$ is Cl or Br and/or wherein A is substituted by at least one Cl or Br atom) with a cyanide, preferably with a metal cyanide, such as NaCN, KCN or $Cu_2(CN)_2$, for example in the presence of pyridine, in an inert solvent, such as DMF or N-methylpyrrolidone, and at temperatures between 20° and 200°.

A base of the formula I can be converted into the appropriate acid addition salt by means of an acid. For this reaction, it is possible to use inorganic acids, for example sulfuric acid, nitric acid, hydrogen halide acids, such as hydrochloric acid or hydrobromic acid, phosphoric acids, such as orthophosphoric acid, or sulfamic acid, and also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, 3-phenylpropionic acid, citric acid, gluconic acid, ascorbic acid, nicotinic acid, isonicotinc acid, methanesulfonic acid, ethanesulfonic acid, ethanedisulfonic acid, 2-hydroxyethanesulfonic acid, benzenesulfonic acid, p-toluenesulfonic acid, naphthalenemonosulfonic acid, naphthalene disulfonic acid and laurylsulfuric acid.

Conversely, it is possible to liberate the base of the formula I from an acid addition salt of a compound of the formula I by treatment with a base, for example with a strong inorganic base, such as KOH or NaOH.

For all the reactions involved in the preparations of compounds of this invention, all starting materials are known and/or readily preparable using fully conventional methods which in turn use known and/or readily preparable materials.

The dielectrics according to the invention consist of 2 to 15, preferably 3 to 12, components, including at least one compound of the formula I. The other constituents are preferably selected from the nematic or nematogenic substances, especially the known substances, belonging to the classes comprising azoxybenzenes, benzylideneanilines, biphenyls, terphenyls, phenyl benzoates, cyclohexyl benzoates, phenyl or cyclohexyl esters of cyclohexanecarboxylic acid, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines, cyclohexylpyrimidines, phenyldioxanes, cyclohexyldioxanes, optionally halogenated stilbenes, benzyl phenyl ethers, tolanes and substituted cinnamic acids.

The most important compounds which are suitable as constituents of liquid-crystal dielectrics of this type are of the formula VI

    VI wherein L and E are each a carbocyclic or heterocyclic ring system composed of the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene, tetrahydronaphthalene, quinazotine and tetrahydroquinazoline; G is

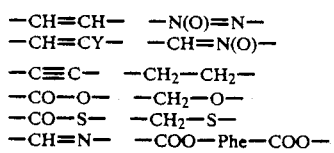

or a C—C single bond, Y is halogen, preferably chlorine, or —CN, and $R^5$ and $R^6$ are alkyl, alkoxy, alkanoyloxy or alkoxycarbonyloxy having up to 18, preferably up to 8, carbon atoms, or one of these radicals is also CN, NC, $NO_2$, $CF_3$, F, CL or Br.

In most of these compounds $R^5$ and $R^6$ are different from one another, and one of these radicals is in most cases an alkyl or alkoxy group. However, other variants of the scheduled substituents are also customary. Many of such substances or mixtures thereof are obtainable commercially.

The dielectrics according to the invention contain about 0.1 to 100, preferably 10 to 100, % of one or more compounds of the formula I.

The preparation of dielectrics according to the invention is effected in a manner which is in itself customary. As a rule, the components are dissolved in one another, preferably at an elevated temperature.

The liquid-crystal dielectrics according to the invention can be modified by means of suitable additives in such a way that they can be used in all types of liquid-crystal display elements hitherto disclosed.

Additives of this type are known to those skilled in the art and are described in detail in the literature. For example, it is possible to add conducting salts, preferably ethyldimethyldodecylammonium 4-hexyloxybenzoate, tetrabutylammonium tetraphenylboranate or complex salts of crown ethers (compare, for example, I. Haller et al., Mol. Cryst. Liq. Cryst. volume 24, pages 249–258 (1973)), in order to improve the conductivity, or to add dichroic dyestuffs in order to prepare coloured guest-host systems, or to add substances for modifying the dielectric anisotropy, the viscosity and/or the orientation of the nematic phases. Substances of this type are described, for example, in German offenlegungsschriften 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is melting point and c.p. is the clear point of a liquid crystal substance.

"Customary working up" refers to the following: water is added, the mixture is extracted with methylene chloride, the phases are separated, the organic phase is dried and evaporated and the product is purified by crystallization and/or chromatography.

EXAMPLE 1

A solution of 30.1 g of r-1-cyano-1-methoxymethyl-cis-4-(p-methoxybenzoylmethyl)-cyclohexane (obtainable from anisole and cis-4-cyano-4-methoxymethylcyclohexyl-r-1-acetyl chloride in the presence of $AlCl_3$) in 500 ml of THF is hydrogenated over 5 g of 10% Pd-on-C at 40° and 1 bar until 0.2 mol of $H_2$ has been taken up. The mixture is filtered and evaporated to give r-1-cyano-1-methoxymethyl-cis-4-(2-p-methoxyphenylethyl)-cyclohexane.

The following are obtained analogously by reducing the corresponding ketones:

r-1-methyl-1-propyl-cis-4-(2-p-methoxyphenylethyl)-cyclohexane
r-1-methyl-1-propyl-cis-4-(2-p-ethoxyphenylethyl)-cyclohexane
r-1-methyl-1-propyl-cis-4-(2-p-ethylphenylethyl)-cyclohexane
r-1-methyl-1-propyl-cis-4-(2-p-cyanophenylethyl)-cyclohexane
r-1-methyl-1-propyl-cis-4-(4'-ethyl-4-biphenylyl)-cyclohexane (from the 4'-acetyl compound).

EXAMPLE 2

A solution of 4.62 g of r-1-p-toluenesulfonyloxymethyl-1-butyl-cis-4-(trans-4-butylcyclohexyl)-cyclohexane [m.p. 95°–97°; obtainable by hydrolysing r-1-cyano-1-butyl-cis-4-(trans-4-butylcyclohexyl)-cyclohexane (see below) to give the carboxylic acid, reducing the latter with $LiAlH_4$ to give r-1-hydroxymethyl-1butyl-cis-4-(trans-4-butylcyclohexyl)-cyclohexane and tosylating the product] in 30 ml of THF is added at 10 to a suspension of 0.5 g of $LiAlH_4$ in 15 ml of THF, and the mixture is boiled for 16 hours. Working up in the customary manner gives r-1-methyl-1-butyl-cis-4-(trans-4-butylcyclohexyl)-cyclohexane, m.p. 0°, c.p. 85°.

The following are obtained analogously by reducing the corresponding tosylates:

r-1-methyl-1-propyl-cis-4-(trans-4-propylcyclohexyl)-cyclohexane
r-1-methyl-1-propyl-cis-4-(trans-4-butylcyclohexyl)-cyclohexane
r-1-methyl-1-propyl-cis-4-(trans-4-pentylcyclohexyl)-cyclohexane
r-1-methyl-1-propyl-cis-4-(trans-4-hexylcyclohexyl)-cyclohexane
r-1-methyl-1-propyl-cis-4-(trans-4-heptylcyclohexyl)-cyclohexane
r-1-methyl-1-butyl-cis-4-(trans-4-propylcyclohexyl)-cyclohexane
r-1-methyl-1-butyl-cis-4-(trans-4-butylcyclohexyl)-cyclohexane
r-1-methyl-1-butyl-cis-4-(trans-4-pentylcyclohexyl)-cyclohexane
r-1-methyl-1-butyl-cis-4-(trans-4-hexylcyclohexyl)-cyclohexane
r-1-methyl-1-butyl-cis-4-(trans-4-heptylcyclohexyl)-cyclohexane
r-1-methyl-1-pentyl-cis-4-(trans-4-propylcyclohexyl)-cyclohexane
r-1-methyl-1-pentyl-cis-4-(trans-4-butylcyclohexyl)-cyclohexane
r-1-methyl-1-pentyl-cis-4-(trans-4-pentylcyclohexyl)-cyclohexane
r-1-methyl-1-pentyl-cis-4-(trans-4-hexylcyclohexyl)-cyclohexane
r-1-methyl-1-pentyl-cis-4-(trans-4-heptylcyclohexyl)-cyclohexane
r-1-methyl-1-hexyl-cis-4-(trans-4-propylcylohexyl)-cyclohexane
r-1-methyl-1-hexyl-cis-4-(trans-4-butylcyclohexyl)-cyclohexane
r-1-methyl-1-hexyl-cis-4-(trans-4-pentylcyclohexyl)-cyclohexane
r-1-methyl-1-hexyl-cis-4-(trans-4-hexylcyclohexyl)-cyclohexane
r-1-methyl-1-hexyl-cis-4-(trans-4-heptylcyclohexyl)-cyclohexane
r-1-methyl-1-heptyl-cis-4-(trans-4-propylcyclohexyl)-cyclohexane
r-1-methyl-1-heptyl-cis-4-(trans-4-butylcyclohexyl)-cyclohexane
r-1-methyl-1-heptyl-cis-4-(trans-4-pentylcyclohexyl)-cyclohexane
r-1-methyl-1-heptyl-cis-4-(trans-4-hexylcyclohexyl)-cyclohexane
r-1-methyl-1-heptyl-cis-4-(trans-4-heptylcyclohexyl)-cyclohexane.

EXAMPLE 3

A mixture of 27.4 g of r-1-acetyl-1-propyl-cis-4-p-methoxyphenylcyclohexane (obtainable from r-1-cyano-1-propyl-cis-4-p-methoxyphenylcyclohexane and $CH_3MgI$), 15 g of KOH, 30 ml of 85% hydrazine and 250 ml of triethylene glycol is heated at 120° for 1 hour. The temperature is raised until the resulting hydrazone has been decomposed, and the mixture is boiled for a further 4 hours, cooled and worked up in the customary manner to give r-1-ethyl-1-propyl-cis-4-p-methoxyphenylcyclohexane.

The following are obtained analogously by Wolff-Kishner reduction of the corresponding ketones:

r-1-methyl-1-propyl-cis-4-(trans-4-p-ethylphenylcyclohexyl)-cyclohexane
(from the p-acetylphenyl compound)
r-1-ethyl-1-propyl-cis-4-(trans-4-propylcyclohexyl)-cyclohexane
r-1-ethyl-1-propyl-cis-4-(trans-4-butylcyclohexyl)-cyclohexane
r-1-ethyl-1-propyl-cis-4-(trans-4-pentylcyclohexyl)-cyclohexane
r-1-ethyl-1-propyl-cis-4-(trans-4-hexylcyclohexyl)-cyclohexane
r-1-ethyl-1-propyl-cis-4-(trans-4-heptylcyclohexyl)-cyclohexane
r-1-ethyl-1-butyl-cis-4-(trans-4-propylcyclohexyl)-cyclohexane
r-1-ethyl-1-butyl-cis-4-(trans-4-butylcyclohexyl)-cyclohexane
r-1-ethyl-1-butyl-cis-4-(trans-4-pentylcyclohexyl)-cyclohexane
r-1-ethyl-1-butyl-cis-4-(trans-4-hexylcyclohexyl)-cyclohexane
r-1-ethyl-1-butyl-cis-4-(trans-4-heptylcyclohexyl)-cyclohexane
r-1-ethyl-1-pentyl-cis-4-(trans-4-propylcyclohexyl)-cyclohexane
r-1-ethyl-1-pentyl-cis-4-(trans-4-butylcyclohexyl)-cyclohexane
r-1-ethyl-1-pentyl-cis-4-(trans-4-pentylcyclohexyl)-cyclohexane
r-1-ethyl-1-pentyl-cis-4-(trans-4-hexylcyclohexyl)-cyclohexane
r-1-ethyl-1-pentyl-cis-4-(trans-4-heptylclohexyl)-cyclohexane
r-1-ethyl-1-hexyl-cis-4-(trans-4-propylcyclohexyl)-cyclohexane
r-1-ethyl-1-hexyl-cis-4-(trans-4-butylcyclohexyl)-cyclohexane
r-1-ethyl-1-hexyl-cis-4-(trans-4-pentylcyclohexyl)-cyclohexane
r-1-ethyl-1-hexyl-cis-4-(trans-4-hexylcyclohexyl)-cyclohexane
r-1-ethyl-1-hexyl-cis-4-(trans-4-heptylcyclohexyl)-cyclohexane
r-1-ethyl-1-heptyl-cis-4-(trans-4-propylcyclohexyl)-cyclohexane
r-1-ethyl-1-heptyl-cis-4-(trans-4-butylcyclohexyl)-cyclohexane
r-1-ethyl-1-heptyl-cis-4-(trans-4-pentylcyclohexyl)-cyclohexane
r-1-ethyl-1-heptyl-cis-4-(trans-4-hexylcyclohexyl)-cyclohexane
r-1-ethyl-1-heptyl-cis-4-(trans-4-heptylcyclohexyl)-cyclohexane
1,1-dipropyl-4-(trans-4-propylcyclohexyl)-cyclohexane.

EXAMPLE 4

A solution of 30.4 g of r-1-fluoro-1-pentyl-cis-4-(2-p-methoxyphenylvinyl)-cyclohexane [obtainable by reacting 4-fluoro-4-pentylcyclohexylmagnesium bromide with p-methoxyphenylacetaldehyde, subsequently hydrolysing the product to give r-1-fluoro-1-pentyl-cis-4-(2-p-methoxyphenyl-1-hydroxethyl)-cyclohexane and dehydrating the latter with p-toluenesulfonic acid in boiling toluene] in 600 ml of THF is hydrogenated over 5 g of PdO at 40° and 1 bar until 0.1 mol of $H_2$ has been taken up. The mixture is filtered and evaporated to give r-1-fluoro-1-pentyl-cis-4-(2-p-methoxyphenylethyl)-cyclohexane.

The following are obtained analogously by hydrogenating the corresponding ethylene derivatives or cyclohexene derivatives:

r-1-chloro-1-pentyl-cis-4-(2-p-methoxyphenylethyl)-cyclohexane
r-1-bromo-1-pentyl-cis-4-(2-p-methoxyphenylethyl)-cyclohexane
r-1-methyl-1-propyl-cis-4-p-methoxyphenyl-cyclohexane (from 1-p-methoxyphenyl-4-methyl-4-propyl-cyclohexane)
r-1-methyl-1-butyl-cis-4-p-methoxyphenyl-cyclohexane
r-1-methyl-1-pentyl-cis-4-p-methoxyphenyl-cyclohexane
r-1-methyl-1-hexyl-cis-4-p-methoxyphenyl-cyclohexane
r-1-methyl-1-heptyl-cis-4-p-methoxyphenyl-cyclohexane
r-1-methyl-1-propyl-cis-4-p-ethoxyphenyl-cyclohexane
r-1-methyl-1-butyl-cis-4-p-ethoxyphenyl-cyclohexane
r-1-methyl-1-pentyl-cis-4-p-ethoxyphenyl-cyclohexane
r-1-methyl-1-hexyl-cis-4-p-ethoxyphenyl-cyclohexane
r-1-methyl-1-heptyl-cis-4-p-ethoxyphenyl-cyclohexane
r-1-methyl-1-propyl-cis-4-p-ethylphenyl-cyclohexane
r-1-methyl-1-butyl-cis-4-ethylphenyl-cyclohexane
r-1-methyl-1-pentyl-cis-4-p-ethylphenyl-cyclohexane
r-1-methyl-1-hexyl-cis-4-p-ethylphenyl-cyclohexane
r-1-methyl-1-heptyl-cis-4-p-ethylphenyl-cyclohexane
r-1-methyl-1-propyl-cis-4-p-cyanophenyl-cyclohexane
r-1-methyl-1-butyl-cis-4-p-cyanophenyl-cyclohexane
r-1-methyl-1-pentyl-cis-4-p-cyanophenyl-cyclohexane
r-1-methyl-1-hexyl-cis-4-p-cyanophenyl-cyclohexane
r-1-methyl-1-heptyl-cis-4-p-cyanophenyl-cyclohexane
r-1-methyl-1-propyl-cis-4-[trans-4-(trans-4-propylcyclohexyl)-cyclohexyl]-cyclohexane.

EXAMPLE 5

HBr is passed, at 0°, into a solution in 50 ml of $CH_2Cl_2$ of 2.42 g of 1-propyl-4-p-propylphenyl-cyclohexene (obtainable by reacting 4-p-propylphenyl-cyclohexanone with $C_3H_7MgBr$, hydrolysing the product to give 1-propyl-4-p-propylphenylcyclohexan-1-ol and dehydrating the latter), the mixture is allowed to stand overnight and is worked up in the customary manner to give r-1-bromo-1-propyl-cis-4-p-propylphenylcyclohexane.

The following are obtained analogously by an addition reaction between HCl or HBr and the corresponding cyclohexenes:

r-1-chloro-1-pentyl-cis-4-p-methoxyphenylcyclohexane
and
r-1-bromo-1-pentyl-cis-4-p-methoxyphenylcyclohexane.

EXAMPLE 6

30.4 g of 1-pentyl-4-(trans-4-pentylcyclohexyl)-cyclohexene [obtainable by reacting 4-(trans-4-pentylcyclohexyl)-cyclohexanone with pentyl-MgBr, hydrolysing the product to give 1-pentyl-4-(trans-4-pentylcyclohexyl)-cyclohexanol and dehydrating the latter], 2.7 g of liquid HCN, 0.1 g of palladium bis-[2,3,0-isopropylidene-2,3-dihydroxy-1,4-bis-(diphenylphosphino)-butane] and 100 ml of acetonitrile are heated at 130° for 1 hour in an autoclave. The mixture is cooled, evaporated and worked up in the customary manner to give r-1-cyano-1-pentyl-cis-4-(trans-4-pentylcyclohexyl)-cyclohexane, m.p. 28°, c.p. 63°.

The following are obtained analogously by an addition reaction between HCN and the corresponding cyclohexene derivatives:

r-1-cyano-1-propyl-cis-4-(4-propyl-1-piperidyl)-cyclohexane
r-1-cyano-1-propyl-cis-4-(4-butyl-1-piperidyl)-cyclohexane
r-1-cyano-1-propyl-cis-4-(4-pentyl-1-piperidyl)-cyclohexane
r-1-cyano-1-propyl-cis-4-(4-hexyl-1-piperidyl)-cyclohexane
r-1-cyano-1-propyl-cis-4-(4-heptyl-1-piperidyl)-cyclohexane
r-1-cyano-1-butyl-cis-4-(4-propyl-1-piperidyl)-cyclohexane
r-1-cyano-1-butyl-cis-4-(4-butyl-1-piperidyl)-cyclohexane
r-1-cyano-1-butyl-cis-4-(4-pentyl-1-piperidyl)-cyclohexane
r-1-cyano-1-butyl-cis-4-(4-hexyl-1-piperidyl)-cyclohexane
r-1-cyano-1-butyl-cis-4-(4-heptyl-1-piperidyl)-cyclohexane
r-1-cyano-1-pentyl-cis-4-(4-propyl-1-piperidyl)-cyclohexane
r-1-cyano-1-pentyl-cis-4-(4-butyl-1-piperidyl)-cyclohexane
r-1-cyano-1-pentyl-cis-4-(4-pentyl-1-piperidyl)-cyclohexane
r-1-cyano-1-pentyl-cis-4-(4-hexyl-1-piperidyl)-cyclohexane
r-1-cyano-1-pentyl-cis-4-(4-heptyl-1-piperidyl)-cyclohexane
r-1-cyano-1-hexyl-cis-4-(4-propyl-1-piperidyl)-cyclohexane
r-1-cyano-1-hexyl-cis-4-(4-butyl-1-piperidyl)-cyclohexane
r-1-cyano-1-hexyl-cis-4-(4-pentyl-1-piperidyl)-cyclohexane
r-1-cyano-1-hexyl-cis-4-(4-hexyl-1-piperidyl)-cyclohexane
r-1-cyano-1-hexyl-cis-4-(4-heptyl-1-piperidyl)-cyclohexane
r-1-cyano-1-heptyl-cis-4-(4-propyl-1-piperidyl)-cyclohexane
r-1-cyano-1-heptyl-cis-4-(4-butyl-1-piperidyl)-cyclohexane
r-1-cyano-1-heptyl-cis-4-(4-pentyl-1-piperidyl)-cyclohexane
r-1-cyano-1-heptyl-cis-4-(4-hexyl-1-piperidyl)-cyclohexane
r-1-cyano-1-heptyl-cis-4-(4-heptyl-1-piperidyl)-cyclohexane
r-1-cyano-1-propyl-cis-4-(4-propyl-bicyclo[2,2,2]octyl)-cyclohexane
r-1-cyano-1-propyl-cis-4-(4-butyl-bicyclo[2,2,2]octyl)-cyclohexane
r-1-cyano-1-propyl-cis-4-(4-pentyl-bicyclo[2,2,2]octyl)-cyclohexane
r-1-cyano-1-propyl-cis-4-(4-hexyl-bicyclo[2,2,2]octyl)-cyclohexane
r-1-cyano-1-propyl-cis-4-(4-heptyl-bicyclo[2,2,2]octyl)-cyclohexane
r-1-cyano-1-butyl-cis-4-(4-propyl-bicyclo[2,2,2]octyl)-cyclohexane
r-1-cyano-1-butyl-cis-4-(4-butyl-bicyclo[2,2,2]octyl)-cyclohexane
r-1-cyano-1-butyl-cis-4-(4-pentyl-bicyclo[2,2,2]octyl)-cyclohexane
r-1-cyano-1-butyl-cis-4-(4-hexyl-bicyclo[2,2,2]octyl)-cyclohexane
r-1-cyano-1-butyl-cis-4-(4-heptyl-bicyclo[2,2,2]octyl)-cyclohexane
r-1-cyano-1-pentyl-cis-4-(4-propyl-bicyclo[2,2,2]octyl)-cyclohexane
r-1-cyano-1-pentyl-cis-4-(4-butyl-bicyclo[2,2,2]octyl)-cyclohexane
r-1-cyano-1-pentyl-cis-4-(4-pentyl-bicyclo[2,2,2]octyl)-cyclohexane
r-1-cyano-1-pentyl-cis-4-(4-hexyl-bicyclo[2,2,2]octyl)-cyclohexane
r-1-cyano-1-pentyl-cis-4-(4-heptyl-bicyclo[2,2,2]octyl)-cyclohexane
r-1-cyano-1-hexyl-cis-4-(4-propyl-bicyclo[2,2,2]octyl)-cyclohexane
r-1-cyano-1-hexyl-cis-4-(4-butyl-bicyclo[2,2,2]octyl)-cyclohexane
r-1-cyano-1-hexyl-cis-4-(4-pentyl-bicyclo[2,2,2]octyl)-cyclohexane
r-1-cyano-1-hexyl-cis-4-(4-hexyl-bicyclo[2,2,2]octyl)-cyclohexane
r-1-cyano-1-hexyl-cis-4-(4-heptyl-bicyclo[2,2,2]octyl)-cyclohexane
r-1-cyano-1-heptyl-cis-4-(4-propyl-bicyclo[2,2,2]octyl)-cyclohexane
r-1-cyano-1-heptyl-cis-4-(4-butyl-bicyclo[2,2,2]octyl)-cyclohexane
r-1-cyano-1-heptyl-cis-4-(4-pentyl-bicyclo[2,2,2]octyl)-cyclohexane
r-1-cyano-1-heptyl-cis-4-(4-hexyl-bicyclo[2,2,2]octyl)-cyclohexane
r-1-cyano-1-heptyl-cis-4-(4-heptyl-bicyclo[2,2,2]octyl)-cyclohexane.

EXAMPLE 7

17 g of trans-4-propylcyclohexanecarboxylic acid are boiled with 24 g of $SOCl_2$ for 1 hour, the mixture is evaporated, the resulting crude acid chloride is dissolved in 150 ml of toluene, 8 ml of pyridine and 16.7 g of cis-4-cyano-4-propylcyclohexanol (obtainable by alkylating 4-cyanocyclohexanol) and the mixture is boiled for 2 hours. Cooling and working up in the customary manner gives cis-4-cyano-4-propylcyclohexyl trans-4-propylcyclohexanecarboxylate.

The following are obtained analogously by esterifying the corresponding acids:

cis-4-cyano-4-butylcyclohexyl trans-4-propylcyclohexanecarboxylate
cis-4-cyano-4-pentylcyclohexyl trans-4-propylcyclohexanecarboxylate
cis-4-cyano-4-hexylcyclohexyl trans-4-propylcyclohexanecarboxylate
cis-4-cyano-4-heptylcyclohexyl trans-4-propylcyclohexanecarboxylate cis-4-cyano-4-propylcyclohexyl trans-4-butylcyclohexanecarboxylate
cis-4-cyano-4-butylcyclohexyl trans-4-butylcyclohexanecarboxylate
cis-4-cyano-4-pentylcyclohexyl trans-4-butylcyclohexanecarboxylate
cis-4-cyano-4-hexylcyclohexyl trans-4-butylcyclohexanecarboxylate
cis-4-cyano-4-heptylcyclohexyl trans-4-butylcyclohexanecarboxylate
cis-4-cyano-4-propylcyclohexyl trans-4-pentylcyclohexanecarboxylate
cis-4-cyano-4-butylcyclohexyl trans-4-pentylcyclohexanecarboxylate
cis-4-cyano-4-pentylcyclohexyl trans-4-pentylcyclohexanecarboxylate
cis-4-cyano-4-hexylcyclohexyl trans-4-pentylcyclohexanecarboxylate
cis-4-cyano-4-heptylcyclohexyl trans-4-pentylcyclohexanecarboxylate
cis-4-cyano-4-propylcyclohexyl trans-4-hexylcyclohexanecarboxylate
cis-4-cyano-4-butylcyclohexyl trans-4-hexylcyclohexanecarboxylate
cis-4-cyano-4-pentylcyclohexyl trans-4-hexylcyclohexanecarboxylate
cis-4-cyano-4-hexylcyclohexyl trans-4-hexylcyclohexanecarboxylate
cis-4-cyano-4-heptylcyclohexyl trans-4-hexylcyclohexanecarboxylate
cis-4-cyano-4-propylcyclohexyl trans-4-heptylcyclohexanecarboxylate
cis-4-cyano-4-butylcyclohexyl trans-4-heptylcyclohexanecarboxylate
cis-4-cyano-4-pentylcyclohexyl trans-4-heptylcyclohexanecarboxylate
cis-4-cyano-4-hexylcyclohexyl trans-4-heptylcyclohexanecarboxylate
cis-4-cyano-4-heptylcyclohexyl trans-4-heptylcyclohexanecarboxylate
trans-4-propylcyclohexyl cis-4-cyano-4-propylcyclohexanecarboxylate
trans-4-butylcyclohexyl cis-4-cyano-4-propylcyclohexanecarboxylate
trans-4-pentylcyclohexyl cis-4-cyano-4-propylcyclohexanecarboxylate
trans-4-hexylcyclohexyl cis-4-cyano-4-propylcyclohexanecarboxylate
trans-4-heptylcyclohexyl cis-4-cyano-4-propylcyclohexanecarboxylate
trans-4-propylcyclohexyl cis-4-cyano-4-butylcyclohexanecarboxylate
trans-4-butylcyclohexyl cis-4-cyano-4-butylcyclohexanecarboxylate
trans-4-pentylcyclohexyl cis-4-cyano-4-butylcyclohexanecarboxylate
trans-4-hexylcyclohexyl cis-4-cyano-4-butylcyclohexanecarboxylate
trans-4-heptylcyclohexyl cis-4-cyano-4-butylcyclohexanecarboxylate
trans-4-propylcyclohexyl cis-4-cyano-4-pentylcyclohexanecarboxylate
trans-4-butylcyclohexyl cis-4-cyano-4-pentylcyclohexanecarboxylate
trans-4-pentylcyclohexyl cis-4-cyano-4-pentylcyclohexanecarboxylate
trans-4-hexylcyclohexyl cis-4-cyano-4-pentylcyclohexanecarboxylate
trans-4-heptylcyclohexyl cis-4-cyano-4-pentylcyclohexanecarboxylate
trans-4-propylcyclohexyl cis-4-cyano-4-hexylcyclohexanecarboxylate
trans-4-butylcyclohexyl cis-4-cyano-4-hexylcyclohexanecarboxylate
trans-4-pentylcyclohexyl cis-4-cyano-4-hexylcyclohexanecarboxylate
trans-4-hexylcyclohexyl cis-4-cyano-4-hexylcyclohexanecarboxylate
trans-4-heptylcyclohexyl cis-4-cyano-4-hexylcyclohexanecarboxylate
trans-4-propylcyclohexyl cis-4-cyano-4-heptylcyclohexanecarboxylate
trans-4-butylcyclohexyl cis-4-cyano-4-heptylcyclohexanecarboxylate
trans-4-pentylcyclohexyl cis-4-cyano-4-heptylcyclohexanecarboxylate
trans-4-hexylcyclohexyl cis-4-cyano-4-heptylcyclohexanecarboxylate
trans-4-heptylcyclohexyl cis-4-cyano-4-heptylcyclohexanecarboxylate
cis-4-cyano-4-propylcyclohexyl p-methoxybenzoate
cis-4-cyano-4-butylcyclohexyl p-methoxybenzoate
cis-4-cyano-4-pentylcyclohexyl p-methoxybenzoate
cis-4-cyano-4-hexylcyclohexyl p-methoxybenzoate
cis-4-cyano-4-heptylcyclohexyl p-methoxybenzoate
cis-4-cyano-4-propylcyclohexyl p-ethoxybenzoate
cis-4-cyano-4-butylcyclohexyl p-ethoxybenzoate
cis-4-cyano-4-pentylcyclohexyl p-ethoxybenzoate
cis-4-cyano-4-hexylcyclohexyl p-ethoxybenzoate
cis-4-cyano-4-heptylcyclohexyl p-ethoxybenzoate
cis-4-cyano-4-propylcyclohexyl p-propoxybenzoate
cis-4-cyano-4-butylcyclohexyl p-propoxybenzoate
cis-4-cyano-4-pentylcyclohexyl p-propoxybenzoate
cis-4-cyano-4-hexylcyclohexyl p-propoxybenzoate
cis-4-cyano-4-heptylcyclohexyl p-propoxybenzoate
cis-4-cyano-4-propylcyclohexyl p-butoxybenzoate
cis-4-cyano-4-butylcyclohexyl p-butoxybenzoate
cis-4-cyano-4-pentylcyclohexyl p-butoxybenzoate
cis-4-cyano-4-hexylcylohexyl p-butoxybenzoate
cis-4-cyano-4-heptylcyclohexyl p-butoxybenzoate
cis-4-cyano-4-propylcyclohexyl p-propylbenzoate
cis-4-cyano-4-butylcyclohexyl p-propylbenzoate
cis-4-cyano-4-pentylcyclohexyl p-propylbenzoate
cis-4-cyano-4-hexylcyclohexyl p-propylbenzoate
cis-4-cyano-4-heptylcyclohexyl p-propylbenzoate
cis-4-cyano-4-propylcyclohexyl p-butylbenzoate
cis-4-cyano-4-butylcyclohexyl p-butylbenzoate
cis-4-cyano-4-pentylcyclohexyl p-butylbenzoate
cis-4-cyano-4-hexylcyclohexyl p-butylbenzoate
cis-4-cyano-4-heptylcyclohexyl p-butylbenzoate
cis-4-cyano-4-propylcyclohexyl p-pentylbenzoate
cis-4-cyano-4-butylcyclohexyl p-pentylbenzoate
cis-4-cyano-4-pentylcyclohexyl p-pentylbenzoate
cis-4-cyano-4-hexylcyclohexyl p-pentylbenzoate
cis-4-cyano-4-heptylcyclohexyl p-pentylbenzoate
p-methoxyphenyl cis-4-cyano-4-propylcyclohexanecarboxylate
p-ethoxyphenyl cis-4-cyano-4-propylcyclohexanecarboxylate
p-propoxyphenyl cis-4-cyano-4-propylcyclohexanecarboxylate
p-butoxyphenyl cis-4-cyano-4-propylcyclohexanecarboxylate
p-propylphenyl cis-4-cyano-4-propylcyclohexanecarboxylate p-butylphenyl cis-4-cyano-4-propylcyclohexanecarboxylate p-pentylphenyl cis-4-cyano-4-propylcyclohexanecarboxylate p-methoxyphenyl cis-4-cyano-4-butylcyclohexanecarboxyate p-ethoxyphenyl cis-4-cyano-4-butylcyclohexanecarboxylate p-propoxyphenyl cis-4-cyano-4-butylcyclohexanecarboxylate p-butoxyphenyl cis-4-cyano-4-butylcyclohexanecarboxylate p-propylphenyl cis-4-cyano-4-butylcyclohexanecarboxylate p-butylphenyl cis-4-cyano-4-butylcyclohexanecarboxylate p-pentylphenyl cis-4-cyano-4-butylcyclohexanecarboxylate p-methoxyphenyl cis-4-cyano-4-pentylcyclohexanecarboxylate p-ethoxyphenyl cis-4-cyano-4-pentylcyclohexanecarboxylate p-propoxyphenyl cis-4-cyano-4-pentylcyclohexancarboxylate p-butoxyphenyl cis-4-cyano-4-pentylcyclohexanecarboxylate p-propylphenyl cis-4-cyano-4-pentylcyclohxanecarboxylate p-butyphenyl cis-4-cyano-4-pentylcyclohexanecarboxylate p-pentylphenyl cis-4-cyano-4-pentylcyclohexanecarboxylate p-methoxyphenyl cis-4-cyano-4-hexylcyclohexanecarboxylate p-ethoxyphenyl cis-4-cyano-4-hexylcyclohexanecarboxylate p-propoxyphenyl cis-4-cyano-4-hexylcyclohexanecarboxylate p-butoxyphenyl cis-4-cyano-4-hexylcyclohexanecarboxylate p-propylphenyl cis-4-cyano-4-hexylcyclohexanecarboxylate p-butylphenyl cis-4-cyano-4-hexylcyclohexanecarboxylate p-pentylphenyl cis-4-cyano-4-hexylcyclohexanecarboxylate p-methoxyphenyl cis-4-cyano-4-heptylcyclohexanecarboxylate p-ethoxyphenyl cis-4-cyano-4-heptylcyclohexanecarboxylate p-propoxyphenyl cis-4-cyano-4-heptylcyclohexanecarboxylate p-butoxyphenyl cis-4-cyano-4-heptylcyclohexanecarboxylate p-propylphenyl cis-4-cyano-4-heptylcyclohexanecarboxylate p-butylphenyl cis-4-cyano-4-heptylcyclohexanecarboxylate p-pentylphenyl cis-4-cyano-4-heptylcyclohexanecarboxylate p-methoxyphenyl r-1-methyl-1-propyl-cyclohexane-cis-4-carboxylate p-ethoxyphenyl r-1-methyl-1-propyl-cyclohexane-cis-4-carboxylate trans-4-propylcyclohexyl r-1-methyl-1-propyl-cyclohexane-cis-4-carboxylate trans-4-pentylcyclohexyl r-1-methyl-1-propyl-cyclohexane-cis-4-carboxylate r-1-cyano-1-propyl-cis-4-(trans-4-acetoxycyclohexyl)-cyclohexane r-1-cyano-1-propyl-cis-4-(trans-4-propionyloxycyclohexyl)-cyclohexane r-1-cyano-1-propyl-cis-4-(trans-4-butyryloxycyclohexyl)-cyclohexane r-1-cyano-1-propyl-cis-4-(trans-4-valeryloxycyclohexyl)-cyclohexane r-1-cyano-1-propyl-cis-4-(trans-4-caproyloxycyclohexyl)-cyclohexane.

EXAMPLE 8

A mixture of 1.2 g of 2-propylpropane-1,3-diol, 1.79 g of 1-cyano-1-propyl-4-formylcyclohexane (obtainable by alkylating 1-cyano-4-formylcyclohexane with propyl bromide), 0.01 g of p-toluenesulfonic acid and 15 ml of toluene is boiled for 3 hours under a water separator and is cooled, washed with water and evaporated. This gives 1-r-cyano-1-propyl-cis-4-(trans-5-propyl-1,3-dioxan-2yl)-cyclohexane.

The following are obtained analogously by reacting the corresponding aldehydes with the corresponding diols:

1-r-cyano-1-propyl-cis-4-(trans-5-butyl-1,3-dioxan-2-yl)-cyclohexane 1-r-cyano-1-propyl-cis-4-(trans-5-pentyl-1,3-dioxan-2-yl)-cyclohexane 1-r-cyano-1-propyl-cis-4-(trans-5-hexyl-1,3-dioxan-2-yl)-cyclohexane 1-r-cyano-1-propyl-cis-4-(trans-5-heptyl-1,3-dioxan-2yl)-cyclohexane 1-r-cyano-1-butyl-cis-4-(trans-5-propyl-1,3-dioxan-2-yl)-cyclohexane 1-r-cyano-1-butyl-cis-4-(trans-5-butyl-1,3-dioxan-2-yl)-cyclohexane 1-r-cyano-1-butyl-cis-4-(trans-5-pentyl-1,3-dioxan-2-yl)-cyclohexane 1-r-cyano-1-butyl-cis-4-(trans-5-hexyl-1,3-dioxan-2-yl)-cyclohexane 1-r-cyano-1-butyl-cis-4-(trans-5-heptyl-1,3-dioxan-2-yl)-cyclohexane 1-r-cyano-1-pentyl-cis-4-(trans-5-propyl-1,3-dioxan-2-yl)-cyclohexane 1-r-cyano-1-pentyl-cis-4-(trans-5-butyl-1,3-dioxan-2-yl)-cyclohexane 1-r-cyano-1-pentyl-cis-4-(trans-5-pentyl-1,3-dioxan-2-yl)-cyclohexane 1-r-cyano-1-pentyl-cis-4-(trans-5-hexyl-1,3-dioxan-2-yl)-cyclohexane 1-r-cyano-1-pentyl-cis-4-(trans-5-heptyl-1,3-dioxan-2-yl)-cyclohexane 1-r-cyano-1-hexyl-cis-4-(trans-5-propyl-1,3-dioxan-2-yl)-cyclohexane 1-r-cyano-1-hexyl-cis-4-(trans-5-butyl-1,3-dioxan-2-yl)-cyclohexane 1-r-cyano-1-hexyl-cis-4-(trans-5-pentyl-1,3-dioxan-2-yl)-cyclohexane 1-r-cyano-1-hexyl-cis-4(trans-5-hexyl-1,3-dioxan-2-yl)-cyclohexane 1-r-cyano-1-hexyl-cis-4-(trans-5-heptyl-1,3-dioxan-2-yl)-cyclohexane 1-r-cyano-1-heptyl-cis-4-(trans-5-propyl-1,3-dioxan-2-yl)-cyclohexane 1-r-cyano-1-heptyl-cis-4-(trans-5-butyl-1,3-dioxan-2-yl)-cyclohexane 1-r-cyano-1-heptyl-cis-4-(trans-5-propyl-1,3-dioxan-2-yl)-cyclohexane 1-r-cyano-1-heptyl-cis-4-(trans-5-pentyl-1,3-dioxan-2-yl)-cyclohexane 1-r-cyano-1-heptyl-cis-4-(trans-5-hexyl-1,3-dioxan-2yl)-cyclohexane 1-r-cyano-1-heptyl-cis-4-(trans-5-heptyl-1,3-dioxan-2yl)-cyclohexane.

EXAMPLE 9

65 g of POCl$_3$ are added dropwise at 50°, stirring, to a solution of 34.9 g of r-1-carbamoyl-1-pentyl-cis-4-(trans-4-pentylcyclohexyl)-cyclohexane (obtainable from the acid chloride by means of NH$_3$) in 500 ml of DMF. After stirring for a further hour, the mixture is poured onto ice and worked up in the customary manner to give r-1-cyano-1-pentyl-cis-4-(trans-4-pentylcyclohexyl)-cyclohexane, m.p. 28°, c.p. 63°.

The following are obtained analogously by eliminating the elements of water from the corresponding amides:

1-r-methyl-1-propyl-cis-4-(4'-cyano-4-biphenyl)-cyclohexane 1-r-methyl-1-propyl-cis-4-(trans-4-p-cyanophenylcyclohexyl)-cyclohexane 1-r-methyl-1propyl-cis-4-[trans-4-cyanocyclohexyl)-cyclohexyl]-cyclohexane.

EXAMPLE 10

A solution of 36.9 g of 1-pentyl-cis-4-(trans-4-pentylcyclohexyl)-cyclohexane-r-1-carbonyl chloride [obtainable by reacting 4-(4-pentylcyclohexyl)-cyclohexanone with pentyl-Li and subsequently hydrolyzing the product to give 1-pentyl-4-(4-pentylcyclohexyl)-cyclohexanol, reacting the latter with K and then with CO$_2$ to give 1-pentyl-cis-4-(trans-4-pentylcyclohexyl)-cyclohexane-r-1-carboxylic acid and reacting the SOCl$_2$] and 8 g of sulfamide in 500 ml of tetramethylene sulfone is heated at 120° for 4 hours, evaporated and worked up in the customary manner. This gives r-1-cyano-1-pentyl-cis-4-(trans-4-pentylcyclohexyl)-cyclohexane, m.p. 28°, c.p. 63°.

EXAMPLE 11

6 g of NaH (50% in paraffin), followed by a solution of 25.3 g of 1,5-dibromopentane in 50 ml of dioxane, are added, with stirring, to a solution, in 150 ml of dimethyl sulfoxide, of 26.3 g of 4'-pentylbiphenylyl-4-acetonitrile [m.p. 80°, c.p. −10°; obtainable from 4-acetyl-4'-pentylbiphenyl via 4'-pentylbiphenylyl-4-acetic acid (m.p. 160°) and the corresponding amide (m.p. 185°)]; the temperature is kept below 35° during the addition by cooling. The mixture is stirred for a further 2 hours, isopropanol is added and working up is carried out in the usual manner. This gives 1-cyano-1-(4'-pentyl-4-biphenylyl)-cyclohexane, m.p. 64°.

The following are obtained analogously from the corresponding acetonitriles and the corresponding 1,5-dibromopentanes:

1-r-cyano-1-(trans-4-propylcyclohexyl)-cis-4-propylcyclohexane;

1-r-cyano-1-(trans-4-propylcyclohexyl)-cis-4-butylcyclohexane 1-r-cyano-1-(trans-4-propylcyclohexyl)-cis-4-pentylcyclohexane, m.p. 45°, c.p. 25°

1-r-cyano-1-(trans-4-propylcyclohexyl)-cis-4-hexylcyclohexane 1-r-cyano-1-(trans-4-propylcyclohexyl)-cis-4-heptylcyclohexane 1-r-cyano-1-(trans-4-butylcyclohexyl)-cis-4-propylcyclohexane 1-r-cyano-1-(trans-4-butylcyclohexyl)-cis-4-butylcyclohexane 1-r-cyano-1-(trans-4-butylcyclohexyl)-cis-4-pentylcyclohexane 1-r-cyano-1-(trans-4-butylcyclohexyl)-cis-4-hexylcyclohexane 1-r-cyano-1-(trans-4-butylcyclohexyl)-cis-4-heptylcyclohexane 1-r-cyano-1-(trans-4-pentylcyclohexyl)-cis-4-propylcyclohexane 1-r-cyano-1-(trans-4-pentylcyclohexyl)-cis-4-butylcyclohexane 1-r-cyano-1-(trans-4-pentylcyclohexyl)-cis-4-pentylcyclohexane 1-r-cyano-1-(trans-4-pentylcyclohexyl)-cis-4-hexylcyclohexane 1-r-cyano-1-(trans-4-pentylcyclohexyl)-cis-4-heptylcyclohexane 1-r-cyano-1-(trans-4-hexylcylohexyl)-cis-4-propylcyclohexane 1-r-cyano-1-(trans-4-hexylcylohexyl)-cis-4-butylcyclohexane 1-r-cyano-1-(trans-4-hexylcyclohexyl)-cis-4-pentylcyclohexane 1-r-cyano-1-(trans-4-hexylcyclohexyl)-cis-4-hexylcyclohexane 1-r-cyano-1-(trans-4-hexylcyclohexyl)-cis-4-heptylcyclohexane 1-r-cyano-1-(trans-4-heptylcyclohexyl)-cis-4-propylcyclohexane 1-r-cyano-1-(trans-4-heptylcyclohexyl)-cis-4-butylcyclohexane 1-r-cyano-1-(trans-4-heptylcyclohexyl)-cis-4-pentylcyclohexane 1-r-cyano-1-(trans-4-heptylcyclohexyl)-cis-4-hexylcyclohexane 1-r-cyano-1-(trans-4-heptylcyclohexyl)-cis-4-heptylcyclohexane r-1-cyano-1-(p-methoxyphenyl)-cis-4-propylcyclohexane r-1-cyano-1-(p-methoxyphenyl)-cis-4-butylcyclohexane r-1-cyano-1-(p-methoxyphenyl)-cis-4-pentylcyclohexane r-1-cyano-1-(p-methoxyphenyl)-cis-4-hexylcyclohexane r-1-cyano-1-(p-methoxyphenyl)-cis-4-heptylcyclohexane r-1-cyano-1-(p-ethoxyphenyl)-cis-4-propylcyclohexane r-1-cyano-1-(p-ethoxyphenyl)-cis-4-butylcyclohexane r-1-cyano-1-(p-ethoxyphenyl)-cis-4-pentylcyclohexane r-1-cyano-1-(p-ethoxyphenyl)-cis-4-hexylcyclohexane r-1-cyano-1-(p-ethoxyphenyl)-cis-4-heptylcyclohexane r-1-cyano-1-(p-propoxyphenyl)-cis-4-propylcyclohexane r-1-cyano-1-(p-propoxyphenyl)-cis-4-butylcyclohexane r-1-cyano-1-(p-propoxyphenyl)-cis-4-pentylcyclohexane r-1-cyano-1-(p-propoxyphenyl)-cis-4-hexylcyclohexane r-1-cyano-1-(p-propoxyphenyl)-cis-4-heptylcyclohexane r-1-cyano-1-(p-butoxyphenyl)-cis-4-propylcyclohexane r-1-cyano-1-(p-butoxyphenyl)-cis-4-butylcyclohexane r-1-cyano-1-(p-butoxyphenyl)-cis-4-pentylcyclohexane r-1-cyano-1-(p-butoxyphenyl)-cis-4-hexylcyclohexane r-1-cyano-1-(p-butoxyphenyl)-cis-4-heptylcyclohexane r-1-cyano-1-(p-propylphenyl)-cis-4-propylcyclohexane
r-1-cyano-1-(p-propylphenyl)-cis-4-butylcyclohexane
r-1-cyano-1-(p-propylphenyl)-cis-4-pentylcyclohexane
r-1-cyano-1-(p-propylphenyl)-cis-4-hexylcyclohexane
r-1-cyano-1-(p-propylphenyl)-cis-4-heptylcyclohexane
r-1-cyano-1-(p-butylphenyl)-cis-4-propylcyclohexane
r-1-cyano-1-(p-butylphenyl)-cis-4-butylcyclohexane
r-1-cyano-1-(p-butylphenyl)-cis-4-pentylcyclohexane
r-1-cyano-1-(p-butylphenyl)-cis-4-hexylcyclohexane
r-1-cyano-1-(p-butylphenyl)-cis-4-heptylcyclohexane
r-1-cyano-1-(p-pentylphenyl)-cis-4-propylcyclohexane
r-1-cyano-1-(p-pentylphenyl)-cis-4-butylcyclohexane
r-1-cyano-1-(p-pentylphenyl)-cis-4-pentylcyclohexane
r-1-cyano-1-(p-pentylphenyl)-cis-4-hexylcyclohexane
r-1-cyano-1-(p-pentylphenyl)-cis-4-heptylcyclohexane
r-1-cyano-1-(2-fluoro-4-methoxyphenyl)-cis-4-propylcyclohexane
r-1-cyano-1-(2-fluoro-4-methoxyphenyl)-cis-4-butylcyclohexane
r-1-cyano-1-(2-fluoro-4-methoxyphenyl)-cis-4-pentylcyclohexane
r-1-cyano-1-(2-fluoro-4-methoxyphenyl)-cis-4-hexylcyclohexane
r-1-cyano-1-(2-fluoro-4-methoxyphenyl)-cis-4-heptylcyclohexane
r-1-cyano-1-(2,3,5,6-tetrafluoro-4-methoxyphenyl)-cis-4-propylcyclohexane
r-1-cyano-1-(2,3,5,6-tetrafluoro-4-methoxyphenyl)-cis-4-butylcyclohexane
r-1-cyano-1-(2,3,5,6-tetrafluoro-4-methoxyphenyl)-cis-4-pentylcyclohexane
r-1-cyano-1-(2,3,5,6-tetrafluoro-4-methoxyphenyl)-cis-4-hexylcyclohexane
r-1-cyano-1-(2,3,5,6-tetrafluoro-4-methoxyphenyl)-cis-4-heptylcyclohexane
r-1-cyano-1-p-fluorophenyl-cis-4-propylcyclohexane
r-1-cyano-1-p-chlorophenyl-cis-4-propylcyclohexane
r-1-cyano-1-p-bromophenyl-cis-4-propylcyclohexane
r-1-cyano-1-(trans-5-propyl-1,3-dioxan-2-yl)-cis-4-propylcyclohexane
r-1-cyano-1-(trans-5-propyl-1,3-dioxan-2-yl)-cis-4-butylcyclohexane
r-1-cyano-1-(trans-5-propyl-1,3-dioxan-2-yl)-cis-4-pentylcyclohexane
r-1-cyano-1-(trans-5-propyl-1,3-dioxan-2-yl)-cis-4-hexylcyclohexane
r-1-cyano-1-(trans-5-propyl-1,3-dioxan-2-yl)-cis-4-heptylcyclohexane
r-1-cyano-1-(trans-5-butyl-1,3-dioxan-2-yl)-cis-4-propylcyclohexane
r-1-cyano-1-(trans-5-butyl-1,3-dioxan-2-yl)-cis-4-butylcyclohexane
r-1-cyano-1-(trans-5-butyl-1,3-dioxan-2-yl)-cis-4-pentylcyclohexane
r-1-cyano-1-(trans-5-butyl-1,3-dioxan-2-yl)-cis-4-hexylcyclohexane
r-1-cyano-1-(trans-5-butyl-1,3-dioxan-2-yl)-cis-4-heptylcyclohexane
r-1-cyano-1-(trans-5-pentyl-1,3-dioxan-2-yl)-cis-4-propylcyclohexane
r-1-cyano-1-(trans-5-pentyl-1,3-dioxan-2-yl)-cis-4-butylcyclohexane
r-1-cyano-1-(trans-5-pentyl-1,3-dioxan-2-yl)-cis-4-pentylcyclohexane
r-1-cyano-1-(trans-5-pentyl-1,3-dioxan-2-yl)-cis-4-hexylcyclohexane
r-1-cyano-1-(trans-5-pentyl-1,3-dioxan-2-yl)-cis-4-heptylcyclohexane
r-1-cyano-1-(trans-5-hexyl-1,3-dioxan-2-yl)-cis-4-propylcyclohexane
r-1-cyano-1-(trans-5-hexyl-1,3-dioxan-2-yl)-cis-4-butylcyclohexane
r-1-cyano-1-(trans-5-hexyl-1,3-dioxan-2-yl)-cis-4-pentylcyclohexane
r-1-cyano-1-(trans-5-hexyl-1,3-dioxan-2-yl)-cis-4-hexylcyclohexane
r-1-cyano-1-(trans-5-hexyl-1,3-dioxan-2-yl)-cis-4-heptylcyclohexane
r-1-cyano-1-(trans-5-heptyl-1,3-dioxan-2-yl)-cis-4-propylcyclohexane
r-1-cyano-1-(trans-5-heptyl-1,3-dioxan-2-yl)-cis-4-butylcyclohexane
r-1-cyano-1-(trans-5-heptyl-1,3-dioxan-2-yl)-cis-4-pentylcyclohexane
r-1-cyano-1-(trans-5-heptyl-1,3-dioxan-2-yl)-cis-4-hexylcyclohexane
r-1-cyano-1-(trans-5-heptyl-1,3-dioxan-2-yl)-cis-4-heptylcyclohexane
r-1-cyano-1-(5-propyl-2-pyrimidyl)-cis-4-propylcyclohexane
r-1-cyano-1-(5-propyl-2-pyrimidyl)-cis-4-butylcyclohexane
r-1-cyano-1-(5-propyl-2-pyrimidyl)-cis-4-pentylcyclohexane
r-1-cyano-1-(5-propyl-2-pyrimidyl)-cis-4-hexylcyclohexane
r-1-cyano-1-(5-propyl-2-pyrimidyl)-cis-4-heptylcyclohexane
r-1-cyano-1-(5-butyl-2-pyrimidyl)-cis-4-propylcyclohexane
r-1-cyano-1-(5-butyl-2-pyrimidyl)-cis-4-butylcyclohexane
r-1-cyano-1-(5-butyl-2-pyrimidyl)-cis-4-pentylcyclohexane
r-1-cyano-1-(5-butyl-2-pyrimidyl)-cis-4-hexylcyclohexane
r-1-cyano-1-(5-butyl-2-pyrimidyl)-cis-4-heptylcyclohexane
r-1-cyano-1-(5-pentyl-2-pyrimidyl)-cis-4-propylcyclohexane
r-1-cyano-1-(5-pentyl-2-pyrimidyl)-cis-4-butylcyclohexane
r-1-cyano-1-(5-pentyl-2-pyrimidyl)-cis-4-pentylcyclohexane
r-1-cyano-1-(5-pentyl-2-pyrimidyl)-cis-4-hexylcyclohexane
r-1-cyano-1-(5-pentyl-2-pyrimidyl)-cis-4-heptylcyclohexane
r-1-cyano-1-(5-hexyl-2-pyrimidyl)-cis-4-propylcyclohexane
r-1-cyano-1-(5-hexyl-2-pyrimidyl)-cis-4-butylcyclohexane
r-1-cyano-1-(5-hexyl-2-pyrimidyl)-cis-4-pentylcyclohexane
r-1-cyano-1-(5-hexyl-2-pyrimidyl)-cis-4-hexylcyclohexane
r-1-cyano-1-(5-hexyl-2-pyrimidyl)-cis-4-heptylcyclohexane
r-1-cyano-1-(5-heptyl-2-pyrimidyl)-cis-4-propylcyclohexane
r-1-cyano-1-(5-heptyl-2-pyrimidyl)-cis-4-butylcyclohexane
r-1-cyano-1-(5-heptyl-2-pyrimidyl)-cis-4-pentylcyclohexane
r-1-cyano-1-(5-heptyl-2-pyrimidyl)-cis-4-hexylcyclohexane r-1-cyano-1-(5-heptyl-2-pyrimidyl)-cis-4-heptylcyclohexane
r-1-cyano-1-(2-propyl-5-pyrimidyl)-cis-4-propylcyclohexane
r-1-cyano-1-(2-propyl-5-pyrimidyl)-cis-4-butylcyclohexane
r-1-cyano-1-(2-propyl-5-pyrimidyl)-cis-4-pentylcyclohexane
r-1-cyano-1-(2-propyl-5-pyrimidyl)-cis-4-hexylcyclohexane
r-1-cyano-1-(2-propyl-5-pyrimidyl)-cis-4-heptylcyclohexane
r-1-cyano-1-(2-butyl-5-pyrimidyl)-cis-4-propylcyclohexane
r-1-cyano-1-(2-butyl-5-pyrimidyl)-cis-4-butylcyclohexane
r-1-cyano-1-(2-butyl-5-pyrimidyl)-cis-4-pentylcyclohexane
r-1-cyano-1-(2-butyl-5-pyrimidyl)-cis-4-hexylcyclohexane
r-1-cyano-1-(2-butyl-5-pyrimidyl)-cis-4-heptylcyclohexane
r-1-cyano-1-(2-pentyl-5-pyrimidyl)-cis-4-propylcyclohexane
r-1-cyano-1-(2-pentyl-5-pyrimidyl)-cis-4-butylcyclohexane
r-1-cyano-1-(2-pentyl-5-pyrimidyl)-cis-4-pentylcyclohexane
r-1-cyano-1-(2-pentyl-5-pyrimidyl)-cis-4-hexylcyclohexane
r-1-cyano-1-(2-pentyl-5-pyrimidyl)-cis-4-heptylcyclohexane
r-1-cyano-1-(2-hexyl-5-pyrimidyl)-cis-4-propylcyclohexane
r-1-cyano-1-(2-hexyl-5-pyrimidyl)-cis-4-butylcyclohexane
r-1-cyano-1-(2-hexyl-5-pyrimidyl)-cis-4-pentylcyclohexane
r-1-cyano-1-(2-hexyl-5-pyrimidyl)-cis-4-hexylcyclohexane
r-1-cyano-1-(2-hexyl-5-pyrimidyl)-cis-4-heptylcyclohexane
r-1-cyano-1-(2-heptyl-5-pyrimidyl)-cis-4-propylcyclohexane
r-1-cyano-1-(2-heptyl-5-pyrimidyl)-cis-4-butylcyclohexane
r-1-cyano-1-(2-heptyl-5-pyrimidyl)-cis-4-pentylcyclohexane
r-1-cyano-1-(2-heptyl-5-pyrimidyl)-cis-4-hexylcyclohexane
r-1-cyano-1-(2-heptyl-5-pyrimidyl)-cis-4-heptylcyclohexane.
r-1-cyano-1-propyl-cis-4-p-methoxyphenyl-cyclohexane
r-1-cyano-1-butyl-cis-4-p-methoxyphenyl-cyclohexane
r-1-cyano-1-pentyl-cis-4-p-methoxyphenyl-cyclohexane
r-1-cyano-1-hexyl-cis-4-p-methoxyphenyl-cyclohexane
r-1-cyano-1-heptyl-cis-4-p-methoxyphenyl-cyclohexane
r-1-cyano-1-propyl-cis-4-p-propylphenyl-cyclohexane
r-1-cyano-1-butyl-cis-4-p-propylphenyl-cyclohexane
r-1-cyano-1-pentyl-cis-4-p-propylphenyl-cyclohexane
r-1-cyano-1-hexyl-cis-4-p-propylphenyl-cyclohexane
r-1-cyano-1-heptyl-cis-4-p-propylphenyl-cyclohexane
r-1-cyano-1-propyl-cis-4-p-butylphenyl-cyclohexane
r-1-cyano-1-butyl-cis-4-p-butylphenyl-cyclohexane
r-1-cyano-1-pentyl-cis-4-butylphenyl-cyclohexane
r-1-cyano-1-hexyl-cis-4-butylphenyl-cyclohexane
r-1-cyano-1-heptyl-cis-4-butylphenyl-cyclohexane
r-1-cyano-1-propyl-cis-4-pentylphenyl-cyclohexane, c.p. 100°
r-1-cyano-1-butyl-cis-4-pentylphenyl-cyclohexane
r-1-cyano-1-pentyl-cis-4-pentylphenyl-cyclohexane
r-1-cyano-1-hexyl-cis-4-pentylphenyl-cyclohexane
r-1-cyano-1-heptyl-cis-4-pentylphenyl-cyclohexane.

EXAMPLE 12

A solution of 5.22 g of diethyl azodicarboxylate in 10 ml of THF is added dropwise, at −20° and while stirring, to a solution of 7.86 g of triphenylphosphine in 200 ml of THF; 1.48 g of 3-methoxymethyl-1,5-pentanediol and 2.09 g of 4-propylcyclohexyl cyanoacetate in 40 ml of THF are then added dropwise. The mixture is stirred for 24 hours at −20°, for a further 24 hours at 0° and for a further 24 hours at 20° and is evaporated and worked up in the customary manner to give trans-4-propylcyclohexyl 1-cyano-trans-4-methoxymethylcyclohexane-r-1-carboxylate.

The following are obtained analogously from the corresponding cyanoacetic acid esters and the corresponding glycols:

trans-4-propylcyclohexyl 1-cyano-trans-4-propylcyclohexane-r-1-carboxylate
trans-4-butylcyclohexyl 1-cyano-trans-4-propylcyclohexane-r-1-carboxylate
trans-4-pentylcyclohexyl 1-cyano-trans-4-propylcyclohexane-r-1-carboxylate
trans-4-hexylcyclohexyl 1-cyano-trans-4-propylcyclohexane-r-1-carboxylate
trans-4-heptylcyclohexyl 1-cyano-trans-4-propylcyclohexane-r-1-carboxylate
p-methoxyphenyl 1-cyano-trans-4-propylcyclohexane-r-1-carboxylate
p-ethoxyphenyl 1-cyano-trans-4-propylcyclohexane-r-1-carboxylate
p-propoxyphenyl 1-cyano-trans-4-propylcyclohexane-r-1-carboxylate
p-butoxyphenyl 1-cyano-trans-4-propylcyclohexane-r-1-carboxylate
p-propylphenyl 1-cyano-trans-4-propylcyclohexane-r-1-carboxylate
p-butylphenyl 1-cyano-trans-4-propylcyclohexane-r-1-carboxylate
p-pentylphenyl 1-cyano-trans-4-propylcyclohexane-r-1-carboxylate
trans-5-propylcyclohexyl 1-cyano-trans-4-butylcyclohexane-r-1-carboxylate
trans-4-butylcyclohexyl 1-cyano-trans-4-butylcyclohexane-r-1-carboxylate
trans-4-pentylcyclohexyl 1-cyano-trans-4-butylcyclohexane-r-1-carboxylate
trans-4-hexylcyclohexyl 1-cyano-trans-4butylcyclohexane-r-1-carboxylate
trans-4-heptylcyclohexyl 1-cyano-trans-4-butylcyclohexane-r-1-carboxylate
p-methoxyphenyl 1-cyano-trans-4-butylcyclohexane-r-1-carboxylate
p-ethoxyphenyl 1-cyano-trans-4-butylcyclohexane-r-1-carboxylate
p-propoxyphenyl 1-cyano-trans-4-butylcyclohexane-r-1-carboxylate
p-butoxyphenyl 1-cyano-trans-4-butylcyclohexane-r-1-carboxylate
p-propylphenyl 1-cyano-trans-4-butylcyclohexane-r-1-carboxylate p-butylphenyl 1-cyano-trans-4-butylcyclohexane-r-1-carboxylate
p-pentylphenyl 1-cyano-trans-4-butylcyclohexane-r-1-carboxylate
trans-4-propylcyclohexyl 1-cyano-trans-4-pentylcyclohexane-r-1-carboxylate
trans-4-butylcyclohexyl 1-cyano-trans-4-pentylcyclohexane-r-1-carboxylate
trans-4-pentylcyclohexyl 1-cyano-trans-4-pentylcyclohexane-r-1-carboxylate
trans-4-hexylcyclohexyl 1-cyano-trans-4-pentylcyclohexane-r-1-carboxylate
trans-4-heptylcyclohexyl 1-cyano-trans-4-pentylcyclohexane-r-1-carboxylate
p-methoxyphenyl 1-cyano-trans-4-pentylcyclohexane-r-1-carboxylate
p-ethoxyphenyl 1-cyano-trans-4-pentylcyclohexane-r-1-carboxylate
p-propoxyphenyl 1-cyano-trans-4-pentylcyclohexane-r-1-carboxylate
p-butoxyphenyl 1-cyano-trans-4-pentylcyclohexane-r-1-carboxylate
p-propylphenyl 1-cyano-trans-4-pentylcyclohexane-r-1-carboxylate
p-butylphenyl 1-cyano-trans-4-pentylcyclohexane-r-1-carboxylate
p-pentylphenyl 1-cyano-trans-4-pentylcyclohexane-r-1-carboxylate
trans-4-propylcyclohexyl 1-cyano-trans-4-hexylcyclohexane-r-1-carboxylate
trans-4-butylcyclohexyl 1-cyano-trans-4-hexylcyclohexane-r-1-carboxylate
trans-4-pentylcyclohexyl 1-cyano-trans-4-hexylcyclohexane-r-1-carboxylate
trans-4-hexylcyclohexyl 1-cyano-trans-4-hexylcyclohexane-r-1-carboxylate
trans-4-heptylcyclohexyl 1-cyano-trans-4-hexylcyclohexane-r-1-carboxylate
p-methoxyphenyl 1-cyano-trans-4-hexylcyclohexane-r-1-carboxylate
p-ethoxyphenyl 1-cyano-trans-4-hexylcyclohexane-r-1-carboxylate
p-propoxyphenyl 1-cyano-trans-4-hexylcyclohexane-r-1-carboxylate
p-butoxyphenyl 1-cyano-trans-4-hexylcyclohexane-r-1-carboxylate
p-propylphenyl 1-cyano-trans-4-hexylcyclohexane-r-1-carboxylate
p-butylphenyl 1-cyano-trans-4-hexylcyclohexane-r-1-carboxylate
p-pentylphenyl 1-cyano-trans-4-hexylcyclohexane-r-1-carboxylate
trans-4-propylcyclohexyl 1-cyano-trans-4-heptylcyclohexane-r-1carboxylate
trans-4-butylcyclohexyl 1-cyano-trans-4-heptylcyclohexane-r-1-carboxylate
trans-4-pentylcyclohexyl 1-cyano-trans-4-heptylcyclohexane-r-1-carboxylate
trans-4-hexylcyclohexyl 1-cyano-trans-4-heptylcyclohexane-r-1-carboxylate
trans-4-heptylcyclohexyl 1-cyano-trans-4-heptylcyclohexane-r-1-carboxylate
p-methoxyphenyl 1-cyano-trans-4-heptylcyclohexane-r-1-carboxylate
p-ethoxyphenyl 1-cyano-trans-4-heptylcyclohexane-r-1-carboxylate
p-propoxyphenyl 1-cyano-trans-4-heptylcyclohexyane-r-1-carboxylate
p-butoxyphenyl 1-cyano-trans-4-heptylcyclohexane-r-1-carboxylate
p-propylphenyl 1-cyano-trans-4-heptylcyclohexane-r-1-carboxylate
p-butylphenyl 1-cyano-trans-4-heptylcyclohexane-r-1-carboxylate
p-pentylphenyl 1-cyano-trans-4-heptylcyclohexane-r-1-carboxylate.

EXAMPLE 13

23.3 g of trans, trans-4-cyano-4'-propylcyclohexylcyclohexane and 41 g of butyl bromide are dissolved in 70 ml of toluene, 4.3 g of NaNH$_2$ (50% mixture with toluene) are added and the mixture is boiled for 5 hours. Working up in the customary manner gives r-1-cyano-1-butyl-cis-4-(trans-4-propylcyclohexyl)-cyclohexane, m.p. 28°, c.p. 28.5°.

The following are obtained analogously by alkylating corresponding nitriles:

r-1-cyano-1-methyl-cis-4-(trans-4-ethylcyclohexyl)-cyclohexane
r-1-cyano-1-methyl-cis-4-(trans-4-propylcyclohexyl)-cyclohexane
r-1-cyano-1-methyl-cis-4-(trans-4-butylcyclohexyl)-cyclohexane
r-1-cyano-1-methyl-cis-4-(trans-4-pentylcyclohexyl)-cyclohexane
r-1-cyano-1-methyl-cis-4-(trans-4-hexylcyclohexyl)-cyclohexane
r-1-cyano-1-methyl-cis-4-(trans-4-heptylcyclohexyl)-cyclohexane
r-1-cyano-1-ethyl-cis-4-(trans-4-ethylcyclohexyl)-cyclohexane, m.p. 41°
r-1-cyano-1-ethyl-cis-4-(trans-4-propylcyclohexyl)-cyclohexane
r-1-cyano-1-ethyl-cis-4-(trans-4-butylcyclohexyl)-cyclohexane
r-1-cyano-1-ethyl-cis-4-(trans-4-pentylcyclohexyl)-cyclohexane
r-1-cyano-1-ethyl-cis-4-(trans-4-hexylcyclohexyl)-cyclohexane
r-1-cyano-1-ethyl-cis-4-(trans-4-heptylcyclohexyl)-cyclohexane, m.p. 41°, c.p. −30°
r-1-cyano-1-propyl-cis-4-(trans-4-methylcyclohexyl)-cyclohexane
r-1-cyano-1-propyl-cis-4-(trans-4-ethylcyclohexyl)-cyclohexane
r-1-cyano-1-propyl-cis-4-(trans-4-propylcyclohexyl)-cyclohexane, m.p. 32°, c.p. 13°
r-1-cyano-1-propyl-cis-4-(trans-4-butylcyclohexyl)-cyclohexane, m.p. 31°, c.p. 27°
r-1-cyano-1-propyl-cis-4-(trans-4-pentylcyclohexyl)-cyclohexane, m.p. 32°, c.p. 42°
r-1-cyano-1-propyl-cis-4-(trans-4-hexylcyclohexyl)-cyclohexane
r-1-cyano-1-propyl-cis-4-(trans-4-heptylcyclohexyl)-cyclohexane, m.p. 38°, c.p. 49°
r-1-cyano-1-propyl-cis-4-(trans-4-octylcyclohexyl)-cyclohexane
r-1-cyano-1-propyl-cis-4-(trans-4-nonylcyclohexyl)-cyclohexane
r-1-cyano-1-propyl-cis-4-(trans-4-decylcyclohexyl)-cyclohexane
r-1-cyano-1-isopropyl-cis-4-(trans-4-heptylcyclohexyl)-cyclohexane, m.p. 73°, c.p. −30°
r-1-cyano-1-butyl-cis-4-(trans-4-methylcyclohexyl)-cyclohexane r-1-cyano-1-butyl-cis-4-(trans-4-ethylcyclohexyl)-cyclohexane
r-1-cyano-1-butyl-cis-4-(trans-4-butylcyclohexyl)-cyclohexane, m.p. 9°, c.p. 36°
r-1-cyano-1-butyl-cis-4-(trans-4-pentylcyclohexyl)-cyclohexane
r-1-cyano-1-butyl-cis-4-(trans-4-hexylcyclohexyl)-cyclohexane
r-1-cyano-1-butyl-cis-4-(trans-4-heptylcyclohexyl)-cyclohexane
r-1-cyano-1-butyl-cis-4-(trans-4-octylcyclohexyl)-cyclohexane
r-1-cyano-1-butyl-cis-4-(trans-4-nonylcyclohexyl)-cyclohexane
r-1-cyano-1-butyl-cis-4-(trans-4-decylcyclohexyl)-cyclohexane
r-1-cyano-1-pentyl-cis-4-(trans-4-methylcyclohexyl)-cyclohexane
r-1-cyano-1-pentyl-cis-4-(trans-4-ethylcyclohexyl)-cyclohexane
r-1-cyano-1-pentyl-cis-4-(trans-4-propylcyclohexyl)-cyclohexane, m.p. 39.5°, c.p. 48.5°
r-1-cyano-1-pentyl-cis-4-(trans-4-butylcyclohexyl)-cyclohexane, m.p. −8°, c.p. 56°
r-1-cyano-1-pentyl-cis-4-(trans-4-pentylcyclohexyl)-cyclohexane, m.p. 28°, c.p. 63°
r-1-cyano-1-pentyl-cis-4-(trans-4-hexylcyclohexyl)-cyclohexane
r-1-cyano-1-pentyl-cis-4-(trans-4-heptylcyclohexyl)-cyclohexane, c.p. 56°
r-1-cyano-1-pentyl-cis-4-(trans-4-octylcyclohexyl)-cyclohexane
r-1-cyano-1-pentyl-cis-4-(trans-4-nonylcyclohexyl)-cyclohexane
r-1-cyano-1-pentyl-cis-4-(trans-4-decylcyclohexyl)-cyclohexane
r-1-cyano-1-hexyl-cis-4-(trans-4-methylcyclohexyl)-cyclohexane
r-1-cyano-1-hexyl-cis-4-(trans-4-ethylcyclohexyl)-cyclohexane
r-1-cyano-1-hexyl-cis-4-(trans-4-propylcyclohexyl)-cyclohexane, m.p. 17°, c.p. 55°
r-1-cyano-1-hexyl-cis-4-(trans-4-butylcyclohexyl)-cyclohexane, m.p. 30°, c.p. 55°
r-1-cyano-1-hexyl-cis-4-(trans-4-pentylcyclohexyl)-cyclohexane
r-1-cyano-1-hexyl-cis-4-(trans-4-hexylcyclohexyl)-cyclohexane
r-1-cyano-1-hexyl-cis-4-(trans-4-heptylcyclohexyl)-cyclohexane
r-1-cyano-1-hexyl-cis-4-(trans-4-octylcyclohexyl)-cyclohexane
r-1-cyano-1-hexyl-cis-4-(trans-4-nonylcyclohexyl)-cyclohexane
r-1-cyano-1-hexyl-cis-4-(trans-4-decylcyclohexyl)-cyclohexane
r-1-cyano-1-heptyl-cis-4-(trans-4-methylcyclohexyl)-cyclohexane
r-1-cyano-1-heptyl-cis-4-(trans-4-ethylcyclohexyl)-cyclohexane
r-1-cyano-1-heptyl-cis-4-(trans-4-propylcyclohexyl)-cyclohexane, m.p. 22°, c.p. 56°
r-1-cyano-1-heptyl-cis-4-(trans-4-butylcyclohexyl)-cyclohexane, m.p. 28°, c.p. 61°
r-1-cyano-1-heptyl-cis-4-(trans-4-pentylcyclohexyl)-cyclohexane, c,p. 50°
r-1-cyano-1-heptyl-cis-4-(trans-4-hexylcyclohexyl)-cyclohexane
r-1-cyano-1-heptyl-cis-4-(trans-4-heptylcyclohexyl)-cyclohexane
r-1-cyano-1-heptyl-cis-4-(trans-4-octylcyclohexyl)-cyclohexane
r-1-cyano-1-heptyl-cis-4-(trans-4-nonylcyclohexyl)-cyclohexane
r-1-cyano-1-heptyl-cis-4-(trans-4-decylcyclohexyl)-cyclohexane
r-1-cyano-1-octyl-cis-4-(trans-4-ethylcyclohexyl)-cyclohexane
r-1-cyano-1-octyl-cis-4-(trans-4-propylcyclohexyl)-cyclohexane, c.p. 50°
r-1-cyano-1-octyl-cis-4-(trans-4-butylcyclohexyl)-cyclohexane
r-1-cyano-1-octyl-cis-4-(trans-4-pentylcyclohexy)-cyclohexane
r-1-cyano-1-octyl-cis-4-(trans-4-hexylcyclohexyl)-cyclohexane
r-1-cyano-1-octyl-cis-4-(trans-4-heptylcyclohexyl)-cyclohexane
r-1-cyano-1-nonyl-cis-4-(trans-4-ethylcyclohexyl)-cyclohexane
r-1-cyano-1-nonyl-cis-4-(trans-4-propylcyclohexyl)-cyclohexane, c.p. 49°
r-1-cyano-1-nonyl-cis-4-(trans-4-butylcyclohexyl)-cyclohexane
r-1-cyano-1-nonyl-cis-4-(trans-4-pentylcyclohexyl)-cyclohexane
r-1-cyano-1-nonyl-cis-4-(trans-4-hexylcyclohexyl)-cyclohexane
r-1-cyano-1-nonyl-cis-4-(trans-4-heptylcyclohexyl)-cyclohexane
r-1-cyano-1-decyl-cis-4-(trans-4-ethylcyclohexyl)-cyclohexane
r-1-cyano-1-decyl-cis-4-(trans-4-propylcyclohexyl)-cyclohexane, m.p. 48°, c.p. 46°
r-1-cyano-1-decyl-cis-4-(trans-4-butylcyclohexyl)-cyclohexane
r-1-cyano-1-decyl-cis-4-(trans-4-pentylcyclohexyl)-cyclohexane
r-1-cyano-1-decyl-cis-4-(trans-4-hexylcyclohexyl)-cyclohexane
r-1-cyano-1-decyl-cis-4-(trans-4-heptylcyclohexyl)-cyclohexane
r-1-cyano-1-methoxymethyl-cis-4-(trans-4-ethylcyclohexyl)-cyclohexane
r-1-cyano-1-methoxymethyl-cis-4-(trans-4-propylcyclohexyl)-cyclohexane
r-1-cyano-1-methoxymethyl-cis-4-(trans-4-butylcyclohexyl)-cyclohexane
r-1-cyano-1-methoxymethyl-cis-4-(trans-4-pentylcyclohexyl)-cyclohexane
r-1-cyano-1-methoxymethyl-cis-4-(trans-4-hexylcyclohexyl)-cyclohexane
r-1-cyano-1-methoxymethyl-cis-4-(trans-4-heptylcyclohexyl)-cyclohexane
r-1-cyano-1-ethoxymethyl-cis-4-(trans-4-pentylcyclohexyl)-cyclohexane, c.p. −50°
r-1-cyano-1-(2,5-dioxahexyl)-cis-4-(trans-4-pentylcyclohexyl)-cyclohexane
r-1-cyano-1-pentyl-2,2-difluoro-cis-4-(trans-4-pentylcyclohexyl)-cyclohexane
r-1-cyano-1-pentyl-cis-4-p-methoxyphenyl-cyclohexane
r-1-cyano-1-[2-(trans-4-propylcyclohexyl)-ethyl]-cis-4-propylcyclohexane
r-1-cyano-1-[2-(trans-4-propylcyclohexyl)-ethyl]-cis-4-butylcyclohexane r-1-cyano-1-[2-(trans-4-propylcyclohexyl)-ethyl]-cis-4-pentylcyclohexane
r-1-cyano-1-[2-(trans-4-propylcyclohexyl)-ethyl]-cis-4-hexylcyclohexane
r-1-cyano-1-[2-(trans-4-propylcyclohexyl)-ethyl]-cis-4-heptylcyclohexane
r-1-cyano-1-[2-(trans-4-butylcyclohexyl)-ethyl]-cis-4-propylcyclohexane
r-1-cyano-1-[2-(trans-4-butylcyclohexyl)-ethyl]-cis-4-butylcyclohexane
r-1-cyano-1-[2-(trans-4-butylcyclohexyl)-ethyl]-cis-4-pentylcyclohexane
r-1-cyano-1-[2-(trans-4-butylcyclohexyl)-ethyl]-cis-4-hexylcyclohexane
r-1-cyano-1-[2-(trans-4-butylcyclohexyl)-ethyl]-cis-4-heptylcyclohexane
r-1-cyano-1-[2-(trans-4-pentylcyclohexyl)-ethyl]-cis-4-propylcyclohexane
r-1-cyano-1-[2-(trans-4-pentylcyclohexyl)-ethyl]-cis-4-butylcyclohexane
r-1-cyano-1-[2-(trans-4-pentylcyclohexyl)-ethyl]-cis-4-pentylcyclohexane
r-1-cyano-1-[2-(trans-4-pentylcyclohexyl)-ethyl]-cis-4-hexylcyclohexane
r-1-cyano-1-[2-(trans-4-pentylcyclohexyl)-ethyl]-cis-4-heptylcyclohexane
r-1-cyano-1-[2-(trans-4-hexylcyclohexyl)-ethyl]-cis-4-propylcyclohexane
r-1-cyano-1-[2-(trans-4-hexylcyclohexyl)-ethyl]-cis-4-butylcyclohexane
r-1-cyano-1-[2-(trans-4-hexylcyclohexyl)-ethyl]-cis-4-pentylcyclohexane
r-1-cyano-1-[2-(trans-4-hexylcyclohexyl)-ethyl]-cis-4-hexylcyclohexane
r-1-cyano-1-[2-(trans-4-hexylcyclohexyl)-ethyl]-cis-4-heptylcyclohexane
r-1-cyano-1-[2-(trans-4-heptylcyclohexyl)-ethyl]-cis-4-propylcyclohexane
r-1-cyano-1-[2-(trans-4-heptylcyclohexyl)-ethyl]-cis-4-butylcyclohexane
r-1-cyano-1-[2-(trans-4-heptylcyclohexyl)-ethyl]-cis-4-pentylcyclohexane
r-1-cyano-1-[2-(trans-4-heptylcyclohexyl)-ethyl]-cis-4-hexylcyclohexane
r-1-cyano-1-[2-(trans-4-heptylcyclohexyl)-ethyl]-cis-4-heptylcyclohexane
r-1-cyano-1-propyl-cis-4-[2-(trans-4-propylcyclohexyl)-ethyl]-cyclohexane
r-1-cyano-1-propyl-cis-4-[2-(trans-4-butylcyclohexyl)-ethyl]-cyclohexane
r-1-cyano-1-propyl-cis-4-[2-(trans-4-pentylcyclohexyl)-ethyl]-cyclohexane
r-1-cyano-1-propyl-cis-4-[2-(trans-4-hexylcyclohexyl)-ethyl]-cyclohexane
r-1-cyano-1-propyl-cis-4-[2-(trans-4-heptylcyclohexyl)-ethyl]-cyclohexane
r-1-cyano-1-butyl-cis-4-[2-(trans-4-propylcyclohexyl)-ethyl]-cyclohexane
r-1-cyano-1-butyl-cis-4-[2-(trans-4-butylcyclohexyl)-ethyl]-cyclohexane
r-1-cyano-1-butyl-cis-4-[2-(trans-4-pentylcyclohexyl)-ethyl]-cyclohexane
r-1-cyano-1-butyl-cis-4-[2-(trans-4-hexylcyclohexyl)-ethyl]-cyclohexane
r-1-cyano-1-butyl-cis-4-[2-(trans-4-heptylcyclohexyl)-ethyl]-cyclohexane
r-1-cyano-1-pentyl-cis-4-[2-(trans-4-propylcyclohexyl)-ethyl]-cyclohexane
r-1-cyano-1-pentyl-cis-4-[2-(trans-4-butylcyclohexyl)-ethyl]-cyclohexane
r-1-cyano-1-pentyl-cis-4-[2-(trans-4-pentylcyclohexyl)-ethyl]-cyclohexane
r-1-cyano-1-pentyl-cis-4-[2-(trans-4-hexylcyclohexyl)-ethyl]-cyclohexane
r-1-cyano-1-pentyl-cis-4-[2-(trans-4-heptylcyclohexyl)-ethyl]-cyclohexane
r-1-cyano-1-hexyl-cis-4-[2-(trans-4-propylcyclohexyl)-ethyl]-cyclohexane
r-1-cyano-1-hexyl-cis-4-[2-(trans-4-butylcyclohexyl)-ethyl]-cyclohexane
r-1-cyano-1-hexyl-cis-4-[2-(trans-4-pentylcyclohexyl)-ethyl]-cyclohexane
r-1-cyano-1-hexyl-cis-4-[2-(trans-4-hexylcyclohexyl)-ethyl]-cyclohexane
r-1-cyano-1-hexyl-cis-4-[2-(trans-4-heptylcyclohexyl)-ethyl]-cyclohexane
r-1-cyano-1-hexyl-cis-4-[2-(trans-4-propylcyclohexyl)-ethyl]-cyclohexane
r-1-cyano-1-heptyl-cis-4-[2-(trans-4-butylcyclohexyl)-ethyl]-cyclohexane
r-1-cyano-1-heptyl-cis-4-[2-(trans-4-pentylcyclohexyl)-ethyl]-cyclohexane
r-1-cyano-1-heptyl-cis-4-[2-(trans-4-hexylcyclohexyl)-ethyl]-cyclohexane
r-1-cyano-1-heptyl-cis-4-[2-(trans-4-heptylcyclohexyl)-ethyl]-cyclohexane
r-1-cyano-1-propyl-cis-4-[2-(trans-4-(trans-4-propylcyclohexyl)-cyclohexyl)-ethyl]-cyclohexane
1-r-cyano-1-propyl-cis-4-[2-(trans-4-(trans-4-pentylcyclohexyl)-cyclohexyl)-ethyl]-cyclohexane
r-1-cyano-1-pentyl-cis-4-[2-(trans-4-(trans-4-propylcyclohexyl)-cyclohexyl)-ethyl]-cyclohexane
r-1-cyano-1-pentyl-cis-4-[2-(trans-4-(trans-4-pentylcyclohexyl)-cyclohexyl)-ethyl]-cyclohexane
r-1-cyano-1-[2-(trans-4-(trans-4-propylcyclohexyl)-cyclohexyl)-ethyl]-cis-4-propyl-cyclohexane
r-1-cyano-1-[2-(trans-4-(trans-4-propylcyclohexyl)-cyclohexyl)-ethyl]-cis-4-pentyl-cyclohexane
r-1-cyano-1-[2-(trans-4-(trans-4-pentylcyclohexyl)-cyclohexyl-ethyl]-cis-4-propyl-cyclohexane
r-1-cyano-1-[2-(trans-4-(trans-pentylcyclohexyl)-cyclohexyl-ethyl]-cis-4-pentyl-cyclohexane
r-1-cyano-1-propyl-cis-4-(trans-4-propylcyclohexylmethoxy)-cyclohexane
r-1-cyano-1-propyl-cis-4-(trans-4-butylcyclohexylmethoxy)-cyclohexane
r-1-cyano-1-propyl-cis-4-(trans-4-pentylcyclohexylmethoxy)-cyclohexane
r-1-cyano-1-propyl-cis-4-(trans-4-hexylcyclohexylmethoxy)-cyclohexane
r-1-cyano-1-propyl-cis-4-(trans-4-heptylcyclohexylmethoxy)-cyclohexane
r-1-cyano-1-butyl-cis-4-(trans-4-propylcyclohexylmethoxy)-cyclohexane
r-1-cyano-1-butyl-cis-4-(trans-4-butylcyclohexylmethoxy)-cyclohexane
r-1-cyano-1-butyl-cis-4-(trans-4-pentylcyclohexylmethoxy)-cyclohexane
r-1-cyano-1-butyl-cis-4-(trans-4-hexylcyclohexylmethoxy)-cyclohexane
r-1-cyano-1-butyl-cis-4-(trans-4-heptylcyclohexylmethoxy)-cyclohexane
r-1-cyano-1-pentyl-cis-4-(trans-4-propylcyclohexylmethoxy)-cyclohexane
r-1-cyano-1-pentyl-cis-4-(trans-4-butylcyclohexylmethoxy)-cyclohexane r-1-cyano-1-pentyl-cis-4-(trans-4-pentylcyclohexylmethoxy)-cyclohexane
r-1-cyano-1-pentyl-cis-4-(trans-4-hexylcyclohexylmethoxy)-cyclohexane
r-1-cyano-1-pentyl-cis-4-(trans-4-heptylcyclohexylmethoxy)-cyclohexane
r-1-cyano-1-hexyl-cis-4-(trans-4-propylcyclohexylmethoxy)-cyclohexane
r-1-cyano-1-hexyl-cis-4-(trans-4-butylcyclohexylmethoxy)-cyclohexane
r-1-cyano-1-hexyl-cis-4-(trans-4-pentylcyclohexylmethoxy)-cyclohexane
r-1-cyano-1-hexyl-cis-4-(trans-4-hexylcyclohexylmethoxy)-cyclohexane
r-1-cyano-1-hexyl-cis-4-(trans-4-heptylcyclohexylmethoxy)-cyclohexane
r-1-cyano-1-heptyl-cis-4-(trans-4-propylcyclohexylmethoxy)-cyclohexane
r-1-cyano-1-heptyl-cis-4-(trans-4-butylcyclohexylmethoxy)-cyclohexane
r-1-cyano-1-heptyl-cis-4-(trans-4-pentylcyclohexylmethoxy)-cyclohexane
r-1-cyano-1-heptyl-cis-4-(trans-4-hexylcyclohexylmethoxy)-cyclohexane
r-1-cyano-1-heptyl-cis-4-(trans-4-heptylcyclohexylmethoxy)-cyclohexane
r-1-cyano-1-propyl-cis-4-(trans-4-propylcyclohexoxymethyl)-cyclohexane
r-1-cyano-1-propyl-cis-4-(trans-4-butylcyclohexoxymethyl)-cyclohexane
r-1-cyano-1-propyl-cis-4-(trans-4-pentylcyclohexoxymethyl)-cyclohexane
r-1-cyano-1-propyl-cis-4-(trans-4-hexylcyclohexoxymethyl)-cyclohexane
r-1-cyano-1-propyl-cis-4-(trans-4-heptylcyclohexoxymethyl)-cyclohexane
r-1-cyano-1-butyl-cis-4-(trans-4-propylcyclohexoxymethyl)-cyclohexane
r-1-cyano-1-butyl-cis-4-(trans-4-butylcyclohexoxymethyl)-cyclohexane
r-1-cyano-1-butyl-cis-4-(trans-4-pentylcyclohexoxymethyl)-cyclohexane
r-1-cyano-1-butyl-cis-4-(trans-4-hexylcyclohexoxymethyl)-cyclohexane
r-1-cyano-1-butyl-cis-4-(trans-4-heptylcyclohexoxymethyl)-cyclohexane
r-1-cyano-1-pentyl-cis-4-(trans-4-propylcyclohexoxymethyl)-cyclohexane
r-1-cyano-1-pentyl-cis-4-(trans-4-butylcyclohexoxymethyl)-cyclohexane
r-1-cyano-1-pentyl-cis-4-(trans-4-pentylcyclohexoxymethyl)-cyclohexane
r-1-cyano-1-pentyl-cis-4-(trans-4-hexylcyclohexoxymethyl)-cyclohexane
r-1-cyano-1-pentyl-cis-4-(trans-4-heptylcyclohexoxymethyl)-cyclohexane
r-1-cyano-1-hexyl-cis-4-(trans-4-propylcyclohexoxymethyl)-cyclohexane
r-1-cyano-1-hexyl-cis-4-(trans-4-butylcyclohexoxymethyl)-cyclohexane
r-1-cyano-1-hexyl-cis-4-(trans-4-pentylcyclohexoxymethyl)-cyclohexane
r-1-cyano-1-hexyl-cis-4-(trans-4-hexylcyclohexoxymethyl)-cyclohexane
r-1-cyano-1-hexyl-cis-4-(trans-4-heptylcyclohexoxymethyl)-cyclohexane
r-1-cyano-1-heptyl-cis-4-(trans-4-propylcyclohexoxymethyl)-cyclohexane
r-1-cyano-1-heptyl-cis-4-(trans-4-butylcyclohexoxymethyl)-cyclohexane
r-1-cyano-1-heptyl-cis-4-(trans-4-pentylcyclohexoxymethyl)-cyclohexane
r-1-cyano-1-heptyl-cis-4-(trans-4-hexylcyclohexoxymethyl)-cyclohexane
r-1-cyano-1-heptyl-cis-4-(trans-4-heptylcyclohexoxymethyl)-cyclohexane
r-1-cyano-1-(trans-4-propylcyclohexoxymethyl)-cis-4-propylcyclohexane
r-1-cyano-1-(trans-4-butylcyclohexoxymethyl)-cis-4-propylcyclohexane
r-1-cyano-1-(trans-4-pentylcyclohexoxymethyl)-cis-4-propylcyclohexane
r-1-cyano-1-(trans-4-hexylcyclohexoxymethyl)-cis-4-propylcyclohexane
r-1-cyano-1-(trans-4-heptylcyclohexoxymethyl)-cis-4-propylcyclohexane
r-1-cyano-1-(trans-4-propylcyclohexoxymethyl)-cis-4-butylcyclohexane
r-1-cyano-1-(trans-4-butylcyclohexoxymethyl)-cis-4-butylcyclohexane
r-1-cyano-1-(trans-4-pentylcyclohexoxymethyl)-cis-4-butylcyclohexane
r-1-cyano-1-(trans-4-hexylcyclohexoxymethyl)-cis-4-butylcyclohexane
r-1-cyano-1-(trans-4-heptylcyclohexoxymethyl)-cis-4-butylcyclohexane
r-1-cyano-1-(trans-4-propylcyclohexoxymethyl)-cis-4-pentylcyclohexane
r-1-cyano-1-(trans-4-butylcyclohexoxymethyl)-cis-4pentylcyclohexane
r-1-cyano-1-(trans-4-pentylcyclohexoxymethyl)-cis-4-pentylcyclohexane
r-1-cyano-1-(trans-4-hexylcyclohexoxymethyl)-cis-4-pentylcyclohexane
r-1-cyano-1-(trans-4-heptylcyclohexoxymethyl)-cis-4-pentylcyclohexane
r-1-cyano-1-(trans-4-propylcyclohexoxymethyl)-cis-4-hexylcyclohexane
r-1-cyano-1-(trans-4-butylcyclohexoxymethyl)-cis-4-hexylcyclohexane
r-1-cyano-1-(trans-4-pentylcyclohexoxymethyl)-cis-4-hexylcyclohexane
r-1-cyano-1-(trans-4-hexylcyclohexoxymethyl)-cis-4-hexylcyclohexane
r-1-cyano-1-(trans-4-heptylcyclohexoxymethyl)-cis-4-hexylcyclohexane
r-1-cyano-1-(trans-4-propylcyclohexoxymethyl)-cis-4-heptylcyclohexane
r-1-cyano-1-(trans-4-butylcyclohexoxymethyl)-cis-4-heptylcyclohexane
r-1-cyano-1-(trans-4-pentylcyclohexoxymethyl)-cis-4-heptylcyclohexane
r-1-cyano-1-(trans-4-hexylcyclohexoxymethyl)-cis-4-heptylcyclohexane
r-1-cyano-1-(trans-4-heptylcyclohexoxymethyl)-cis-4-heptylcyclohexane.

EXAMPLE 14 r-1-Trans-4-dicyano-1,4-bis-(trans-4-propylcyclohexyl)-cyclohexane is obtained analogously to Example 13 from trans-1,4-dicyanocyclohexane and 2 mols of 4-propylcyclohexyl bromide.

The following are obtained analogously using the corresponding bromides:

r-1-trans-4-dicyano-1,4-bis-(trans-4-butylcyclohexyl)-cyclohexane
r-1-trans-4-dicyano-1,4-bis-(trans-4-pentylcyclohexyl)-cyclohexane
r-1-trans-4dicyano-1,4-bis-(trans-4-hexylcyclohexyl)-cyclohexane
r-1-trans-4-dicyano-1,4-bis-(trans-4-heptylcyclohexyl)-cyclohexane
r-1-trans-4-dicyano-1,4-bis-(trans-4-methoxymethylcyclohexyl)-cyclohexane.

The following are obtained analogously using the corresponding 2-cyclohexylethyl or 2-phenylethyl bromides:

r-1-trans-4-dicyano-1,4-bis-[2-(trans-4-propylcyclohexyl)-ethyl]-cyclohexane
r-1-trans-4-dicyano-1,4-bis-[2-(trans-4-butylcyclohexyl)-ethyl]-cyclohexane
r-1-trans-4-dicyano-1,4-bis-[2-(trans-4-pentylcyclohexyl)-ethyl]-cyclohexane
r-1-trans-4-dicyano-1,4-bis-[2-(trans-4-hexylcyclohexyl)-ethyl]-cyclohexane
r-1-trans-4-dicyano-1,4-bis-[2-(trans-4-heptylcyclohexyl)-ethyl]-cyclohexane
r-1-trans-4-dicyano-1,4-bis-2-p-methoxyphenyl-ethyl)-cyclohexane
r-1-trans-4-dicyano-1,4-bis-2-p-ethoxyphenyl-ethyl)-cyclohexane.

EXAMPLE 15

A mixture of 24.3 g of r-1-cyano-1-p-hydroxyphenyl-cis-4-propylcyclohexane, 6.9 g of $K_2CO_3$, 25 g of hexyl iodide and 250 ml of DMF is heated at 80° for 16 hours, while stirring, and is then cooled and worked up in the customary manner. This gives r-1-cyano-1-p-hexoxyphenyl-cis-4-propylcyclohexane.

The following are obtained analogously by etherification:

r-1-cyano-1-p-pentoxyphenyl-cis-4-propylcyclohexane
r-1-cyano-1-p-heptoxyphenyl-cis-4-propylcyclohexane
r-1-cyano-1-p-octoxyphenyl-cis-4-propylcyclohexane
r-1-cyano-1-p-nonoxyphenyl-cis-4-propylcyclohexane
r-1-cyano-1-p-decyloxyphenyl-cis-4-propylcyclohexane.

EXAMPLE 16

4.8 g of NaH and 27.8 g of $CH_3I$ are added to a solution of 29.4 g of r-1-hydroxy-1-pentyl-cis-4-(trans-4-propylcyclohexyl)-cyclohexane [obtainable by oxidising 4-(trans-4-propylcyclohexyl)-cyclohexanol with $CrO_3$ to give the ketone, reacting the latter with pentyl-MgBr and hydrolysing the product] in 280 ml of 1,2-dimethoxyethane. The mixture is heated at 70° for 5 hours and cooled, and the product is decomposed with water and worked up in the customary manner to give r-1-methoxy-1-pentyl-cis-4-(trans-4-propylcyclohexyl)-cyclohexane, m.p. 43°, c.p. 135°.

The following are obtained analogously by etherification:

r-1-methoxy-1-propyl-cis-4-(trans-4-propylcyclohexyl)-cyclohexane
r-1-methoxy-1-propyl-cis-4-(trans-4-butylcyclohexyl)-cyclohexane
r-1-methoxy-1-propyl-cis-4-(trans-4-pentylcyclohexyl)-cyclohexane
r-1-methoxy-1-propyl-cis-4-(trans-4-hexylcyclohexyl)-cyclohexane
r-1-methoxy-1-propyl-cis-4-(trans-4-heptylcyclohexyl)-cyclohexane
r-1-methoxy-1-butyl-cis-4-(trans-4-propylcyclohexyl)-cyclohexane
r-1-methoxy-1-butyl-cis-4-(trans-4-butylcyclohexyl)-cyclohexane
r-1-methoxy-1-butyl-cis-4-(trans-4-pentylcyclohexyl)-cyclohexane
r-1-methoxy-1-butyl-cis-4-(trans-4-hexylcyclohexyl)-cyclohexane
r-1-methoxy-1-butyl-cis-4-(trans-4-heptylcyclohexyl)-cyclohexane
r-1-methoxy-1-pentyl-cis-4-(trans-4-butylcyclohexyl)-cyclohexane
r-1-methoxy-1-pentyl-cis-4-(trans-4-pentylcyclohexyl)-cyclohexane
r-1-methoxy-1-pentyl-cis-4-(trans-4-hexylcyclohexyl)-cyclohexane
r-1-methoxy-1-pentyl-cis-4-(trans-4-heptylcyclohexyl)-cyclohexane
r-1-methoxy-1-hexyl-cis-4-(trans-4-propylcyclohexyl)-cyclohexane
r-1-methoxy-1-hexyl-cis-4-(trans-4-butylcyclohexyl)-cyclohexane
r-1-methoxy-1-hexyl-cis-4-(trans-4-pentylcyclohexyl)-cyclohexane
r-1-methoxy-1-hexyl-cis-4-(trans-4-hexylcyclohexyl)-cyclohexane
r-1-methoxy-1-hexyl-cis-4-(trans-4-heptylcyclohexyl)-cyclohexane
r-1-methoxy-1-heptyl-cis-4-(trans-4-propylcyclohexyl)-cyclohexane
r-1-methoxy-1-heptyl-cis-4-(trans-4-butylcyclohexyl)-cyclohexane
r-1-methoxy-1-heptyl-cis-4-(trans-4-pentylcyclohexyl)-cyclohexane
r-1-methoxy-1-heptyl-cis-4-(trans-4-hexylcyclohexyl)-cyclohexane
r-1-methoxy-1-heptyl-cis-4-(trans-4-heptylcyclohexyl)-cyclohexane
r-1-ethoxy-1-propyl-cis-4-(trans-4-propylcyclohexyl)-cyclohexane
r-1-ethoxy-1-propyl-cis-4-(trans-4-butylcyclohexyl)-cyclohexane
r-1-ethoxy-1-propyl-cis-4-(trans-4-pentylcyclohexyl)-cyclohexane
r-1-ethoxy-1-propyl-cis-4-(trans-4-hexylcyclohexyl)-cyclohexane
r-1-methoxy-1-propyl-cis-4-(trans-4-heptylcyclohexyl)-cyclohexane
r-1-ethoxy-1-butyl-cis-4-(trans-4-propylcyclohexyl)-cyclohexane
r-1-ethoxy-1-butyl-cis-4-(trans-4-butylcyclohexyl)-cyclohexane
r-1-ethoxy-1-butyl-cis-4-(trans-4-pentylcyclohexyl)-cyclohexane
r-1-ethoxy-1-butyl-cis-4-(trans-4-hexylcyclohexyl)-cyclohexane
r-1-ethoxy-1-butyl-cis-4-(trans-4-heptylcyclohexyl)-cyclohexane
r-1-ethoxy-1-pentyl-cis-4-(trans-4-propylcyclohexyl)-cyclohexane
r-1-ethoxy-1-pentyl-cis-4-(trans-4-butylcyclohexyl)-cyclohexane
r-1-ethoxy-1-pentyl-cis-4-(trans-4-pentylcyclohexyl)-cyclohexane r-1-ethoxy-1-pentyl-cis-4-(trans-4-hexylcyclohexyl)-cyclohexane r-1-ethoxy-1-pentyl-cis-4-(trans-4-heptylcyclohexyl)-cyclohexane r-1-ethoxy-1-hexyl-cis-4-(trans-4-propylcyclohexyl)-cyclohexane r-1-ethoxy-1-hexyl-cis-4-(trans-4-butylcyclohexyl)-cyclohexane r-1-ethoxy-1-hexyl-cis-4-(trans-4-pentylcyclohexyl)-cyclohexane r-1-ethoxy-1-hexyl-cis-4-(trans-4-hexylcyclohexyl)-cyclohexane r-1-ethoxy-1-hexyl-cis-4-(trans-4-heptylcyclohexyl)-cyclohexane r-1-ethoxy-1-heptyl-cis-4-(trans-4-propylcyclohexyl)-cyclohexane r-1-ethoxy-1-heptyl-cis-4-(trans-4-butylcyclohexyla)-cyclohexane r-1-ethoxy-1-heptyl-cis-4-(trans-4-pentylcyclohexyl)-cyclohexane r-1-ethoxy-1-heptyl-cis-4-(trans-4-hexylcyclohexyl)-cyclohexane r-1-ethoxy-1-heptyl-cis-4-(trans-4-heptylcyclohexyl)-cyclohexane

EXAMPLE 17

A mixture of 30.6 g of r-1-cyano-1-p-bromophenyl-cis-4-propylcyclohexane, 10 g of $Cu_2(CN)_2$, 120 ml of pyridine and 60 ml of N-methylpyrrolidone is heated at 150° C. for 2 hours. The mixture is cooled, a solution of 120 g of $FeCl_3.6H_2O$ in 600 ml of 20% hydrochloric acid is added, and the mixture is warmed at 70° for 1.5 hours, while stirring, and worked up in the customary manner to give r-1-cyano-1-p-cyanophenyl-cis-4-propylcyclohexane.

EXAMPLE 18

A mixture of 29.4 g of 1-propyl-cis-4-(trans-4-propylcyclohexyl)-cyclohexane-r-1-carboxylic acid (obtainable by hydrolysis of the nitrile), 21.6 g of $SF_4$ and 300 ml of cyclohexane is heated at 150° for 24 hours in a Hastelloy autoclave. After cooling, the pressure is released, the autoclave is evacuated and flushed several times with nitrogen and the reaction mixture is poured onto ice. Working up in the customary manner gives r-1-trifluoromethyl-1-propyl-cis-4-(trans-4-propylcyclohexyl)-cyclohexane.

The following can be obtained analogously from the corresponding carboxylic acids:

r-1-trifluoromethyl-1-propyl-cis-4-(trans-4-butylcyclohexyl)-cyclohexane r-1-trifluoromethyl-1-propyl-cis-4-(trans-4-pentylcyclohexyl)-cyclohexane r-1-trifluoromethyl-1-propyl-cis-4-(trans-4-hexylcyclohexyl)-cyclohexane r-1-trifluoromethyl-1-propyl-cis-4-(trans-4-heptylcyclohexyl)-cyclohexane r-1-trifluoromethyl-1-butyl-cis-4-(trans-4-propylcyclohexyl)-cyclohexane r-1-trifluoromethyl-1-butyl-cis-4-(trans-4-butylcyclohexyl)-cyclohexane r-1-trifluoromethyl-1-butyl-cis-4-(trans-4-pentylcyclohexyl)-cyclohexane r-1-trifluoromethyl-1-butyl-cis-4-(trans-4-hexylcyclohexyl)-cyclohexane r-1-trifluoromethyl-1-butyl-cis-4-(trans-4-heptylcyclohexyl)-cyclohexane 1-trifluoromethyl-1-pentyl-cis-4-(trans-4-propylcyclohexyl)-cyclohexane 1-trifluoromethyl-1-pentyl-cis-4-(trans-4-butylcyclohexyl)-cyclohexane 1-trifluoromethyl-1-pentyl-cis-4-(trans-4-pentylcyclohexyl)-cyclohexane 1-trifluoromethyl-1-pentyl-cis-4-(trans-4-hexylcyclohexyl)-cyclohexane 1-trifluoromethyl-1-pentyl-cis-4-(trans-4-heptylcyclohexyl)-cyclohexane 1-trifluoromethyl-1-hexyl-cis-4-(trans-4-propylcyclohexyl)-cyclohexane 1-trifluoromethyl-1-hexyl-cis-4-(trans-4-butylcyclohexyl)-cyclohexane 1-trifluoromethyl-1-hexyl-cis-4-(trans-4-pentylcyclohexyl)-cyclohexane 1-trifluoromethyl-1-hexyl-cis-4-(trans-4-hexylcyclohexyl)-cyclohexane 1-trifluoromethyl-1-hexyl-cis-4-(trans-4-heptylcyclohexyl)-cyclohexane 1-trifluoromethyl-1-heptyl-cis-4-(trans-4-propylcyclohexyl)-cyclohexane 1-trifluoromethyl-1-heptyl-cis-4-(trans-4-butylcyclohexyl)-cyclohexane 1-trifluoromethyl-1-heptyl-cis-4-(trans-4-pentylcyclohexyl)-cyclohexane 1-trifluoromethyl-1-heptyl-cis-4-(trans-4-hexylcyclohexyl)-cyclohexane 1-trifluoromethyl-1-heptyl-cis-4-(trans-4-heptylcyclohexyl)-cyclohexane.

The following are examples of dielectrics according to the invention containing at least one compound of the formula I:

EXAMPLE A

A mixture of

11% of r-1-cyano-1-pentyl-cis-4-(trans-4-propylcyclohexyl)-cyclohexane

24% of r-1-cyano-1-heptyl-cis-4-(trans-4-propylcyclohexyl)-cyclohexane

21% of r-1-cyano-1-propyl-cis-4-(trans-4-pentylcyclohexyl)-cyclohexane

21% of r-1-cyano-1-pentyl-cis-4-(trans-4-pentylcyclohexyl)-cyclohexane

13% of r-1-cyano-1-propyl-cis-4-(trans-4-heptylcyclohexyl)-cyclohexane

10% of 4-(trans-4-pentylcyclohexyl)-4'-(trans-4-propylcyclohexyl)-biphenyl 15 has m.p. −11° and c.p. 75°.

EXAMPLE B 2 parts by weight of the blue dyestuff 4,8-diamino-1,5-dihydroxy-2-p-methoxyphenylanthraquinone are dissolved in 98 parts by weight of the mixture according to Example A. The order parameter of the dyestuff is 0.71.

EXAMPLE C

A mixture of

9% of r-1-cyano-1-pentyl-cis-4-(trans-4-propylcyclohexyl)-cyclohexane

19% of r-1-cyano-1-heptyl-cis-4-(trans-4-propylcyclohexyl)-cyclohexane

17% of r-1-cyano-1-propyl-cis-4-(trans-4-pentylcyclohexyl)-cyclohexane

17% of r-1-cyano-1-pentyl-cis-4-(trans-4-pentylcyclohexyl)-cyclohexane
10% of r-1-cyano-1-propyl-cis-4-(trans-4-heptylcyclohexyl)-cyclohexane
28% of 4-ethyl-2'-fluoro-4'-(trans-4-pentylcyclohexyl)-biphenyl has m.p. −16° and c.p. 66°.

EXAMPLE D 2 parts by weight of the red dyestuff 1-p-dimethylaminobenzylideneamino-4-p-cyanophenylazonaphthalene are dissolved in 98 parts by weight of the mixture according to Example C. The order parameter of the dyestuff is 0.68.

EXAMPLE E

A mixture of

13% of r-1-cyano-1-pentyl-cis-4-(trans-4-propylcyclohexyl)-cyclohexane
27% of r-1-cyano-1-heptyl-cis-4-(trans-4-propylcyclohexyl)-cyclohexane
23% of r-1-cyano-1-propyl-cis-4-(trans-4-pentylcyclohexyl)-cyclohexane
23% of r-1-cyano-1-pentyl-cis-4-(trans-4-pentylcyclohexyl)-cyclohexane
14% of 1-r-cyano-1-propyl-cis-4-(trans-4-heptylcyclohexyl)-cyclohexane 25 has m.p. −9° and c.p. 52°.

EXAMPLE F 1 part by weight of bis-(p-isopropylphenyl) perylene-3,9-bis-carboxylate is dissolved in 99 parts by weight of the mixture according to Example E. The order parameter of the dyestuff is 0.73.

EXAMPLE G

A mixture of

12% of r-1-cyano-1-pentyl-cis-4-(trans-4-propylcyclohexyl)-cyclohexane
25% of r-1-cyano-1-heptyl-cis-4-(trans-4-propylcyclohexyl)-cyclohexane
22% of r-1-cyano-1-propyl-cis-4-(trans-4-pentylcyclohexyl)-cyclohexane
22% of r-1-cyano-1-pentyl-cis-4-(trans-4-pentylcyclohexyl)-cyclohexane
13% of r-1-cyano-1-propyl-cis-4-(trans-4-heptylcyclohexyl)-cyclohexane
6% of trans-4-propylcyclohexyl trans,trans-4-propylcyclohexylcyclohexane-4'-carboxylate has m.p. −10° and c.p. 59°.

EXAMPLE H

A mixture of

12% of r-1-cyano-1-pentyl-cis-4-(trans-4-propylcyclohexyl)-cyclohexane
24% of r-1-cyano-1-heptyl-cis-4-(trans-4-propylcyclohexyl)-cyclohexane
21% of r-1-cyano-1-propyl-cis-4-(trans-4-pentylcyclohexyl)-cyclohexane
21% of r-1-cyano-1-pentyl-cis-4-(trans-4-pentylcyclohexyl)-cyclohexane
13% of r-1-cyano-1-propyl-cis-4-(trans-4-heptylcyclohexyl)-cyclohexane
9% of p-trans-4-butylcyclohexylphenyl trans-4-pentylcyclohexanecarboxylate has m.p. −11° and c.p. 63°.

EXAMPLE I

A mixture of

19% of r-1-cyano-1-heptyl-cis-4-(trans-4-propylcyclohexyl)-cyclohexane
18% of r-1-cyano-1-pentyl-cis-4-(trans-4-pentylcyclohexyl)-cyclohexane
11% of p-ethoxyphenyl trans-4-propylcyclohexanecarboxylate
9% of 4-(trans-4-pentylcyclohexyl)-4'-(trans-4-propylcyclohexyl)-biphenyl
28% of 4-ethyl-2'-fluoro-4'-(trans-4-pentylcyclohexyl)-biphenyl
15% of trans-1-(p-ethoxyphenyl)-4-propylcyclohexane has m.p. −15° and c.p. 86°.

EXAMPLE J

A mixture of

18% of r-1-cyano-1-heptyl-cis-4-(trans-4-propylcyclohexyl)-cyclohexane
17% of r-1-cyano-1-propyl-cis-4-(trans-4-pentylcyclohexyl)-cyclohexane
17% of r-1-cyano-1-pentyl-cis-4-(trans-4-pentylcyclohexyl)-cyclohexane
10% of r-1-cyano-1-propyl-cis-4-(trans-4-heptylcyclohexyl)-cyclohexane
24% of 4-butyl-2-cyanophenyl p-(trans-4-propylcyclohexyl)-benzoate
14% of trans-1-(p-ethoxyphenyl)-4propylcyclohexane has m.p. −16° and c.p. 63°.

EXAMPLE K

A mixture of

19% of r-1-cyano-1-pentyl-cis-4-(trans-4-propylcyclohexyl)-cyclohexane
31% of r-1-cyano-1-propyl-cis-4-(trans-4-pentylcyclohexyl)-cyclohexane
33% of r-1-cyano-1-pentyl-cis-4-(trans-4-pentylcyclohexyl)-cyclohexane
17% of 4-(trans-4-pentylcyclohexyl)-4'-(trans-4-propylcyclohexyl)-biphenyl has m.p. −2° and c.p. 91°.

EXAMPLE L

A mixture of

11% of r-1-cyano-1-pentyl-cis-4-(trans-4-propylcyclohexyl)-cyclohexane
25% of r-1-cyano-1-heptyl-cis-4-(trans-4-propylcyclohexyl)-cyclohexane
21% of r-1-cyano-1-propyl-cis-4-(trans-4-pentylcyclohexyl)-cyclohexane
22% of r-1-cyano-1-pentyl-cis-4-(trans-4-pentylcyclohexyl)-cyclohexane
13% of r-1-cyano-1-propyl-cis-4-(trans-4-heptylcyclohexyl)-cyclohexane 8% of trans-4-propylcyclohexyl p-(trans-4-propylcyclohexyl)-benzoate has m.p. −11° and c.p. 60°.

EXAMPLE M

A mixture of

22% of r-1-cyano-1-heptyl-cis-4-(trans-4-propylcyclohexyl)-cyclohexane
20% of r-1-cyano-1-pentyl-cis-4-(trans-4-pentylcyclohexyl)-cyclohexane
18% of trans-4-propylcyclohexyl trans-4-pentylcyclohexanecarboxylate
10% of 4-(trans-4-pentylcyclohexyl)-4'-(trans-4-propylcyclohexyl)-biphenyl
30% of 4-ethyl-2'-fluoro-4'-(trans-4-pentylcyclohexyl)-biphenyl has m.p. −12° and c.p. 92°.

EXAMPLE N

A mixture of

17% of r-1-cyano-1-pentyl-cis-4-(trans-4-pentylcyclohexyl)-cyclohexane
43% of trans-4-propylcyclohexyl trans-4-propylcyclohexanecarboxylate
16% of trans-4-propylcyclohexyl trans-4-pentylcyclohexanecarboxylate
17% of 4-butyl-2-cyanophenyl p-(trans-4-propylcyclohexyl)-benzoate has m.p. −16° and c.p. 58°.

EXAMPLE O

A mixture of

9% of 2-p-cyanophenyl-5-propyl-1,3-dioxane
12% of 2-p-cyanophenyl-5-butyl-1,3-dioxane
9% of 2-p-cyanophenyl-5-pentyl-1,3-dioxane
6% of 2-p-octoxyphenyl-5-pentyl-pyrimidine
5% of 2-p-nonoxyphenyl-5-pentyl-pyrimidine
5% of 2-p-heptoxyphenyl-5-hexyl-pyrimidine
4% of 2-p-nonoxyphenyl-5-hexyl-pyrimidine
6% of 4,4'-bis-(trans-4-propylcyclohexyl)-biphenyl
9% of 4-(trans-4-pentylcyclohexyl)-4'-(trans-4-propylcyclohexyl)-biphenyl
17% of r-1-cyano-1-pentyl-cis-4-(trans-4-propylcyclohexyl)-cyclohexane and
18% of r-1-cyano-1-heptyl-cis-4-(trans-4-propylcyclohexyl)-cyclohexane has m.p. −5° and c.p. 66°. This mixture has a particularly steep characteristic line.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystal dielectric useful for electrooptical display elements and comprising at least two liquid crystal components, at least one of which comprises at least one 1,4-cyclohexylene ring, the improvement wherein one 1,4-cyclohexylene ring is additionally substituted in the 1-position, the 4-position or the 1,4-position by alkyl, alkoxy, fluorinated alkyl or fluorinated alkoxy, each of 1–5 C atoms, F, Cl, Br, CN or a combination thereof and is optionally also substituted by 1 or 2 of F, Cl, Br, CN or a combination thereof.

2. In a liquid crystal dielectric useful for electrooptical display elements and comprising at least two liquid crystal components, at least one of which comprises at least one 1,4-cyclohexylene ring, the improvement wherein one 1,4-cyclohexylene ring is additionally substituted in the 1-position, the 4-position or the 1,4-position by alkyl, alkoxy, fluorinated alkyl or fluorinated alkoxy, each of 1–5 C atoms, F, Cl, Br or CN.

3. A dielectric of claim 1, wherein said at least one component comprising said additionally substituted 1,4-cyclohexylene ring comprises at least two six-membered rings.

4. A dielectric of claim 2, wherein said at least one component comprising said additionally substituted 1,4-cyclohexylene ring comprises at least two six-membered rings.

* * * * *